US011427832B2

(12) United States Patent
Suzuki et al.

(10) Patent No.: US 11,427,832 B2
(45) Date of Patent: Aug. 30, 2022

(54) DOWNY MILDEW RESISTANT CABBAGE AND BREEDING METHOD THEREFOR

(71) Applicant: SAKATA SEED CORPORATION, Yokohama (JP)

(72) Inventors: Takao Suzuki, Kanagawa (JP); Atsushi Izumida, Kanagawa (JP); Tetsuya Hiramoto, Kanagawa (JP); Kenji Takebayashi, Kanagawa (JP)

(73) Assignee: SAKATA SEED CORPORATION

( * ) Notice: Subject to any disclaimer, the term of this patent is extended or adjusted under 35 U.S.C. 154(b) by 0 days.

(21) Appl. No.: 16/645,653

(22) PCT Filed: Sep. 11, 2018

(86) PCT No.: PCT/JP2018/035573
§ 371 (c)(1),
(2) Date: Mar. 9, 2020

(87) PCT Pub. No.: WO2019/050042
PCT Pub. Date: Mar. 14, 2019

(65) Prior Publication Data

US 2020/0283791 A1 Sep. 10, 2020

(30) Foreign Application Priority Data

Sep. 11, 2017 (JP) ............................ JP2017-173823

(51) Int. Cl.

| | |
|---|---|
| ***C12N 15/82*** | (2006.01) |
| ***C12Q 1/68*** | (2018.01) |
| ***A01H 5/10*** | (2018.01) |
| ***C12Q 1/6895*** | (2018.01) |
| *A01H 6/20* | (2018.01) |
| *A01H 1/02* | (2006.01) |

(52) U.S. Cl.
CPC ........... *C12N 15/8282* (2013.01); *A01H 5/10* (2013.01); *C12Q 1/6895* (2013.01); *A01H 1/02* (2013.01); *A01H 6/203* (2018.05); *C12Q 2600/13* (2013.01)

(58) Field of Classification Search
None
See application file for complete search history.

(56) References Cited

FOREIGN PATENT DOCUMENTS

| | | |
|---|---|---|
| CN | 101748211 A | 6/2010 |
| KR | 2012-0136772 A | 12/2012 |

OTHER PUBLICATIONS

Lee et al. BMC Plant Biology (2015) 15:32.*
Carlsson et al. Hereditas (2004)141:293-330.*
J.G. Vicente, et al., "Genetics of resistance to downy mildew in *Brassica oleracea* and breeding towards durable disease con trol for UK vegetable production.", Plant Pathology (2012), vol. 61, pp. 600-609 (10 pages).
Claude E. Thomas, et al., "Resistance to Race 2 of Peronospora parasi tica in u. s. Plant Introductions of *Brassica oleracea* var. *capi tata*.", Hort Science, 1992, vol. 27(10), pp. 1120-1122 (3 pages).
Mamoru Satou, et al., "The Host Range of Downy Mildew, *Peronospora parasitica*, from *Brassica oleracea*, Cabbage and Broccoli Crops", Ann. Phytopathol. Soc. Jpn., vol. 62, Published 1996, pp. 393-396 (4 pages).
Janel L. Giovannelli, et al., "Development of Sequence Characterized Amplified Region Markers Linked to Downy Mildew Resistance in Broccoli ", J. Amer. Soc. Hort. Sci., 2002, vol. 127(4), pp. 597-601 (5 pages).
M. Farinho, et al., "Mapping of a locus for adult plant resistance to downy mildew in broccoli (*Brassica oleracea* convar. *Italica*).", Theor. Appl. Genet., 2004, vol. 109, pp. 1392-1398 (7 pages).
Saitama Prefectural Agricultural and Forestry Research, "Comprehensive control of broccoli mildew and diseases that develop in floret"; Website Research Performance Information of "Kanto Tokai Hokuriku Agriculture", 2007 (URL: www.naro.affrc.go.jp/org/narc/seika/kanto19/12/19_12_09.html); retrieved on Nov. 16, 2018 (5 pages) with English abstract.
Naoko Minegishi, "Control of downy mildew on broccoli heads"; Magazine "Plant Protection", 2009, vol. 6, No. 2, pp. 21-25 (6 pages) with English abstract.
International Search Report issued for corresponding International Application No. PCT/JP2018/033573, dated Nov. 27, 2018 (4 pages).
Supplementary European Search Report issued for the corresponding European Patent Application No. 18854890.3 dated Jun. 14, 2021 (total 10 pages).

* cited by examiner

*Primary Examiner* — Medina A Ibrahim
(74) *Attorney, Agent, or Firm* — Harness, Dickey & Pierce, P.L.C.

(57) ABSTRACT

The present application discloses a cabbage having resistance against downy mildew or its progeny. The present application further discloses a method for breeding downy mildew resistant cabbage, including introducing downy mildew resistance from a *Brassica oleracea* plant having resistance against downy mildew into desired cabbage. One embodiment of the present invention provides a novel cabbage line showing high resistance against downy mildew and having a high commercial value as cabbage, and enables breeding such cabbage.

10 Claims, 12 Drawing Sheets

Specification includes a Sequence Listing.

DOWNY MILDEW IN BROCCOLI SEEDLINGS (INOCULATION TEST)

LEFT: SUSCEPTIBLE, RIGHT: RESISTANT

ORIGINAL LINE "CB-20"

ISOGENIC LINE INTRODUCED WITH DOWNY MILDEW RESISTANT FACTOR

F1 VARIETY INTRODUCED WITH DOWNY MILDEW RESISTANCE

ORIGINAL F1 VARIETY

FIG. 8-1

DMTLR-1:

(UNDERLINED PART INDICATES THE PRIMER SITES DESIGNED BY THE PRESENT INVENTION.)
(ENTIRE SEQUENCE REPRESENTS SEQ NO. 22, AND THE PRIMER SITES AND THE SEQUENCE SANDWICHED BETWEEN THEM REPRESENTS SEQ NO. 1.)

CGGTCCTTAGTTGATTTCTCAAGTTTGGGTGTTTGTCCAATCATCTCTTGGTACAGTTGAAGCAAAAGCTTCA
TCTCTGCATATAATACTCAGAACAATCAATAATTTTAAAAAGAAAACAACAGAGTGCTATAATGAGAGAGAGA
GAGAGAGAGAGAGACTCACTCTCTTGAATTTCGACTGCTGCCTTGCAGTTTCTGAAGTCGGGAGCTCGTAG
TACCTATACAATTACCAGAACATATACTCTCCGTTGATATCTAATTAATTCCACAAACAGAGAGAAGAGTAGT
GGAGATTTCATACCTCGAGAACGTGAGGCCGAAGATCCTTGACAAGGAGACGCATCTTGTAGTAGTTGGAGTT
CTCCACCTTCAGATTCCCTTCCAGCCCCCTCTTTCTCCCCCTTGACGACGGATCTGACGGAGCCACCTGAGCT
CCTCCTATATGTGGCCGACTCGGAACCGGCGGGTTATCTAAGTCCATCGCCGGCGAAGATCTCTGATCTGCTG
CAGCTGCTGTAGGAAGCGGGAGAGATGAAGTAGCGGAAGGAGGAGGAGGAGTTGCCGCCGAGGTCGATTTCTC
CATTTTCAAAAAGGGGGTTTTCTCAACCGTAACACCCCAGCACGGGACGCAGCAGCCGGGAACTTAAAACGAC
CGCGTTGTAAGAAATCTACTGATTCGGTTAGGGCCTACTTGGGGGCCCATTATCTTTTTTTCTTTGTCTAAACG
GCCCGTCTGTATCCGATGACCATCATATAGAAGGGTAAATCATCAAGTAACAACAACACTGCAACAGACAAGG
GACATATGTAGCTGAACAGAGAACTCTCTATTCATTAGACTGAGATATATGTTCATAATAAATTAAGTCAAAT
CCTGCATAATAGCTCAAAGCTGGATTTAATCATTCATAATTCCATGAATTTTTTTTTACATAGATATAGTCTTC
AGTTTGACCCCAAAAAAAAAAAATAGTCTTCATATACTCATCTCTCCAAAGTGATTGCTAGTACAGGGTGATC
ATCTTCTAATCTTCACAACAAGTCAAGCATGAGCTGTTCCAGTAATTCATTTAGAATCAGTTCACTAGTCTCA
AAGCCAATGCACTCAACCTCACTTCTAACGTCATCTAACCAGTTTCCGCCGTTTATCCATGTCTTCTCTAATGA
TTTGGTCC

DMTLR-2:

(UNDERLINED PART INDICATES THE PRIMER SITES DESIGNED BY THE PRESENT INVENTION.)
(ENTIRE SEQUENCE REPRESENTS SEQ NO. 23, AND THE PRIMER SITES AND THE SEQUENCE SANDWICHED BETWEEN THEM REPRESENTS SEQ NO. 2)

GAACCCCTCTCGGACCGGGAATAAGATTCTTGGTTTTTCGGTTAAAGTAGGGAGTAAACCAACGAGTGTAAAT
ATCTTCCCCAAGCCGTTCCGGGATGATGTGCAAGGTAAACCAAGTGATGGCTATGGGACAAGGAAAGAAACA
AAATGTTCCTGCATGAAAATATTGAAGTTTGATGCAAACCCACAAATTTGGTATATATTTCAAAGTTATTGGT
TCGTGTTCAAACGGGTATATGCTAACAACCTAATATGCACTCGTGG

FIG. 8-2

DMTLR-3:

(UNDERLINED PART INDICATES THE PRIMER SITES DESIGNED BY THE PRESENT INVENTION.)
(ENTIRE SEQUENCE REPRESENTS SEQ NO. 24, AND THE PRIMER SITES AND THE SEQUENCE SANDWICHED BETWEEN THEM REPRESENTS SEQ NO. 3.)

GTGCTCCGTCAAGATTCGACGATCGTGTTTTGTTTCCCTTTTTACTTTAACTCTCTTCACTCTTCTTCCTTCA
TTCTCCTCTTCTGATGGGAAGCCATAGCAACGCGGAGAAAGATGAATCCGCCACCGAGACGGATGCTACAACA
CGGCAGGGATCTCTCTCTGTTACAGAGTCCAACACCGATTGCGACGCAGACGTCTTGCCTCCTCCTCCTCCTG
CGGACGTGAGTCAATTCGAAGAAGGAGAGAAAGTTTTAGCCAACCACAAAGGTCGTTTCTACGAAGCCAAGGT
AATGTTATTTTTGTCTAAAATTGGAATGTTGTTTGTGCTTTTGTGTTTAAAATTTGATCTTTGTTTTATGTTT
TCAGGTTCTTGAAATTGCATTTAAAGACAATGAATGGAACTATTATGTGCATTACATTGTAAGTTTAGATTTT
ATTTTGTTTTGCGTAACCACGAATCTCTGTAAAAGCATAAACAAATAAAACACATTTATTGTTAATGCTGCCG
TTATTATATTTTTGCCGTTTTCAATATGTAATCTTTTGTATTTTCTTTGGTTTTTACAGGGTTGGAACAAAAG
GTTAGTAGACCATCCGACAGTACTGTCACTTACTGCCGGCTTTTTATTGTCTGAATAATCTTTCTGTACATTG
CATCATCGGTCTGAATAATCATTCTGCTGCTAAATCAAAACGTTTGCCAAGATTACAAGTTTTTTTTGTTTCT
AATGCATTGATAATTTCATGGTTTGATTATTGTTGTATATCTTTGTAATGATTAGTTATTTGTATGGACAGTT
GGGACGAATGGATAGGTCATGATTGTGTGTTGAAACACACCCGAGGAGAATATTAAGGAACAGGGTATTAAGCA
AGGAGTCAAGAGTGCTATGGCTTGGAGAGTGTCCAAGGTGAAACCTAGATGCCCTAATGGTCAGTGTTCTGGG
TCTTTTATTAGAGGCTTTGTTGCATGCTTTATAGATCATATGCTAGATATTATCATCATTCTCTTGTTAATAT
ATTTTGCAGTTGCTAGACGAAGAAAGCGGAAGCAAGATTCTGTTGATACACTAGTCTCTCCAATGGTGTGGAT
TTTCCTTTCATTTTTCTCTAGATTCCAAGTTTCTTTCTATTGTTTTCTGATCAGTTTTTGCCTGATTGTTTTT
GTTGTTTGCTGGATACAGGAGGAGAATTTGGTTGCTACAGACAACCTTTTAACTTTCAATATCCCGTCAGCGT
TGAGGAAGCAACTCATCGACGATTATGAATTCGTTACTCAGATGCAAAAGGTAGCTCTCGATTCATTAGGTCC
ATATATCAAGGAATTTATCAGTGACATTTTTTGTAACATTTATGTGAGCAGCTTGTGGAACTTCCTCGCTCGC
CTAATGTGGATGATATCTTGAAGAAGTACACTGACAGCAAAATGAAGAAAGATGGCAGGTAAGCGCTTTGTTA
ATGTCATTTTCAACAGTTAAAGAGTTATTTCAGTACTTTCTTTTGGTGAGGTTATGTAGGGTAAGCAATTCAG
TAGAGGAGATTCTGAAAGGTTTGCGTTGCTACTTTGACAATGCTTTGCCGGTGATGTTACTTTACAACAATGA
GCGGAAGCAGTATGAGGAAAACGTATCTGAGGGTGTATCTCCCTCAACTGTGT

FIG. 8-3

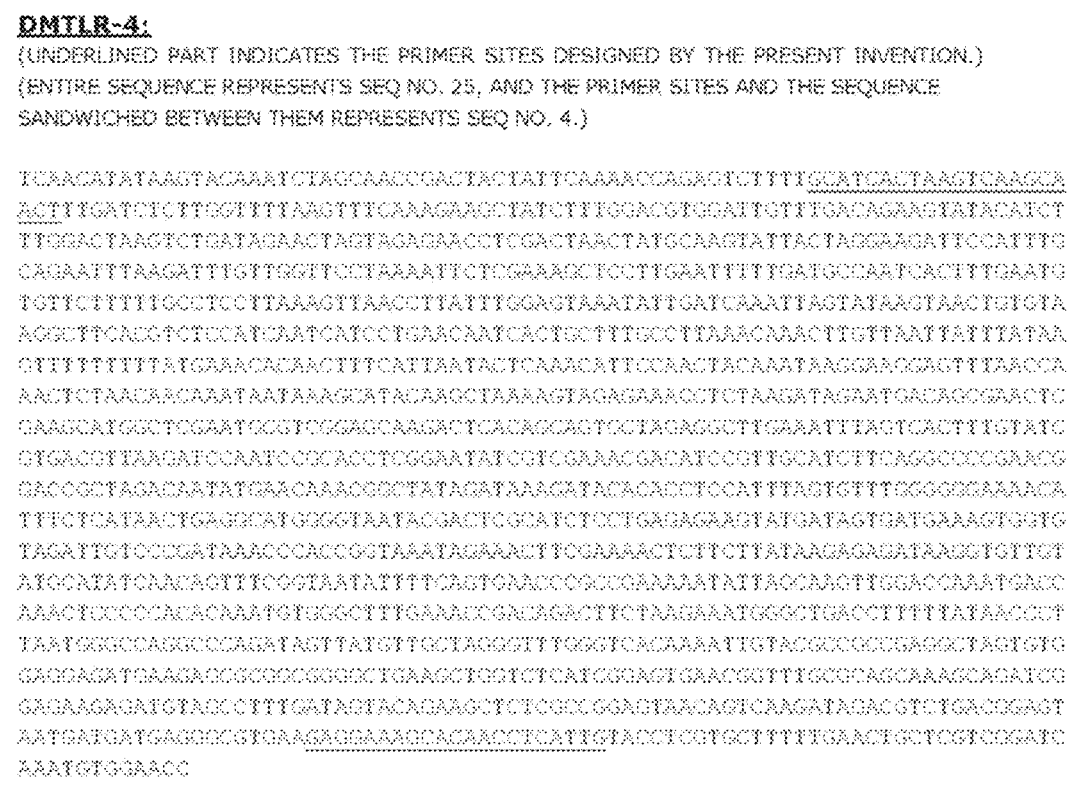

DMTLR-4:

(UNDERLINED PART INDICATES THE PRIMER SITES DESIGNED BY THE PRESENT INVENTION.)
(ENTIRE SEQUENCE REPRESENTS SEQ NO. 25, AND THE PRIMER SITES AND THE SEQUENCE SANDWICHED BETWEEN THEM REPRESENTS SEQ NO. 4.)

TCAACATATAAGTACAAATCTAGCAACCGACTACTATTCAAAACCAGAGTCTTTTGCATCACTAAGTCAAGCA
ACTTTGATCTCTTGGTTTTAAGTTTCAAAGAAGCTATCTTTGGACGTGGATTGTTTGACAGAAGTATACATCT
TTGGACTAAGTCTGATAGAACTAGTAGAGAACCTCGACTAACTATGCAAGTATTACTAGGAAGATTCCATTTG
CAGAATTTAAGATTTGTTGGTTCCTAAAATTCTCGAAAGCTCCTTGAATTTTTGATGCCAATCACTTTGAATG
TGTTCTTTTTGCCTCCTTAAAGTTAACCTTATTTGGAGTAAATATTGATCAAATTAGTATAAGTAACTGTGTA
AGGCTTCACGTCTCCATCAATCATCCTGAACAATCACTGCTTTGCCTTAAACAAACTTGTTAATTATTTATAA
GTTTTTTTTTATGAAACACAACTTTCATTAATACTCAAACATTCCAACTACAAATAAGGAACGAGTTTAACCA
AACTCTAACAACAAATAATAAAGCATACAAGCTAAAAGTAGAGAAACCTCTAAGATAGAATGACAGCGAACTC
GAAGCATGGCTCGAATGCGTCGGAGCAAGACTCACAGCAGTGCTAGAGGCTTGAAATTTAGTCACTTTGTATC
GTGACGTTAAGATCCAATCCGCACCTCGGAATATCGTCGAAACGACATCCGTTGCATCTTCAGGCCCCGAACG
GACCGCTAGACAATATGAACAAACGGCTATAGATAAAGATACACACCTCCATTTAGTGTTTGGGGGGAAAACA
TTTCTCATAACTGAGGCATGGGGTAATACGACTCGCATCTCCTGAGAGAAGTATGATAGTGATGAAAGTGGTG
TAGATTGTCCCGATAAACCCACCGGTAAATAGAAACTTCGAAAACTCTTCTTATAAGAGAGATAAGGTGTTGT
ATGCATATCAACAGTTTCGGTAATATTTTCAGTGAACCCGCCGAAAAATATTAGCAAGTTGGACCAAATGACC
AAACTCCCCCACACAAATGTGGGCTTTGAAACCGACAGACTTCTAAGAAATGGGCTGACCTTTTTATAACCCT
TAATGGGCCAGGCCCAGATAGTTATGTTGCTAGGGTTTGGGTCACAAAATTGTACGCCCGCCGAGGCTAGTGTG
GAGGAGATGAAGACGCGCCGGGGCTGAAGCTGGTCTCATCGGAGTGAACGGTTTGCGCAGCAAAGCAGATCG
GAGAAGAGATGTAGCCTTTGATAGTACAGAAGCTCTCGCCGGAGTAACAGTCAAGATAGACGTCTGACCGAGT
AATGATGATGAGGGCGTGAAGAGGAAAGCACAACCTCATTGTACCTCGTGCTTTTTGAACTGCTCGTCGGATC
AAATGTGGAACC

FIG. 8-4

DMTLR-5:

(UNDERLINED PART INDICATES THE PRIMER SITES DESIGNED BY THE PRESENT INVENTION.)
(ENTIRE SEQUENCE REPRESENTS SEQ NO. 26, AND THE PRIMER SITES AND THE SEQUENCE SANDWICHED BETWEEN THEM REPRESENTS SEQ NO. 5.)

TTTTCAGGTAGTTCCACTCTCATATTATGTATGTTGAGTTTACTGTCCCTATTGAGTTTGTGCAATTTCCTAT
ATATTTCTCTGCAATATTGTCCTTGATGAGTTTATTGTCTCCCTTCTTTTTCAGTAAATTCAGTTTCGTTTTA
TTTATCTATTGAATTTATTGTCGCTATTGAATTTTCTGACGTATTTCTCTGCGATCACTCAATTTACTGTCTC
TGTTGAGTTTCTCATTCTTCCCATTCAGAATATATGTAGAAACAACAATTCAATATAAGTCATCTGTTCGCTC
TATCATAGTAGCGTAAAGGTATCTTTCCAAATTGACTTGGCATCCATATTAGAGAGACGTCAATGAATATAAG
TAGTATTTACAACTAAATTCGTCTGATTTTACAAATGCTTCCAAGCGTACGTGTATACCAATGTTCGCCTAAA
GATAAATGCCAAGGTTGGTGTACTGAATTGCTTGTTAACTATGGAGCGTTCACCAGCAATGCCATTAGTAACA
CAAGTTCCTAGCATTATTGCTGGGATGGATGTACCATCAGTTGATGCGATTGTGAGCTCCATACAATGGCCAC
TCGTATCAAAATAAAGGGCATGTGTGTATGCGTACACAATTGT

DMTLR-6:

(UNDERLINED PART INDICATES THE PRIMER SITES DESIGNED BY THE PRESENT INVENTION.)
(ENTIRE SEQUENCE REPRESENTS SEQ NO. 27, AND THE PRIMER SITES AND THE SEQUENCE SANDWICHED BETWEEN THEM REPRESENTS SEQ NO. 6.)

ATGAGGAGGCTGAAGTGCGCTCGTTTCTGCAGCATACTTCAACTCAAGCTGCAGCAAATGGAAACGATTAGTG
AGGAATGCAACGGAAGCTTCGGCTTCCGAACAAGAACATAGTACATAAAGAGAAGGACACTAAGTACCTTGTC
TCCATGTCCACTGCTGAGGCAATCGGAAACAGGTTTAGAGTTGAGATTGAGCTTCTGATAACAAGTCTCCCAC
TTGTCGTACTTGTGCTCAGTCACCAAACTCTCAACACAGTGGATAAACGGGAAATGATCGCTCTACAAAATAA
AAATGTAACGATCTCACACTAACTAGGCTTCACCAAACAAAAAGATCACAATCAAATCTCATCATCCTACTTA
CCAATTTAGGCCACGCATCAATCGCACAAGCTTCAACTGTATCCAAAAGGCATTCAAACGCACCGTGCTGCAA
CAAATTAGCAACAATGTTTAACGTAATCTCGCTACAAGCATGCATGATAACGAAACGAGATCTTAGATACAAA
CAACATCTTAAATAAATTTAATCAAATTATCGACAATGTTTAATGTAATCGCTACAATCATGCATGATGACGA
AACGAGATCTCAGATTCAAACAACACCACAATACAAATTGAAGCTCTAATTTAATCAAATCAGGATACATCGG
AAAGGTGTGAGAAGACCTGGCAAACGGCAGTGACATTATCGGAGCGGAGCTTGGTGTTACCCCACGGAGATAG
ATGGAGATCGACGATTGATATGAGATCGTCTTCGAAGAGCTTCGTGAGGTGGTTAACGATGAAGGAAGAA

FIG. 8-5

DMTLR-7:

(UNDERLINED PART INDICATES THE PRIMER SITES DESIGNED BY THE PRESENT INVENTION.)

(ENTIRE SEQUENCE REPRESENTS SEQ NO. 28, AND THE PRIMER SITES AND THE SEQUENCE SANDWICHED BETWEEN THEM REPRESENTS SEQ NO. 7.)

CTTACACAACCCAACAACCATACACTTTGTGATATATAGATAATAATTAATACAGATTCATCATATCTCGGAA
TCTATATAGATTTTAGAGAGTTATCATGTTACATATCACAAAAGAAAGAGAAGGTGTTTTATAGAAGGCCTGT
GTACGACAACAAAGAGGTTTTGACACGTTCCAACAAATCCCACATCCTGTTGACACCGTTCCGGCAAACCAGA
GGGAACCGATTCACTTTAGCACTTCGAATGAAGTGGCTGGATGAGTATTTGGCACACGCGTCAGGCTTTTTAG
CACCTTTGTAAGCTTTGCAGATGTAGCTTATGAAGTTCTCATAATCCTGCAATGAACACACAGAAAAAAACTG
TGGTGAGTTCAGAGCCAAGAAATATCAAGCACACACACACACACAAAAACTTTATGTTCCCATTGATCACATCCA
TTTTCTATTGATCATGCCTCTCATGAAGACACTTCACTTCTCGTCTGCTAACTACAGTTCACAAGAACAATAA
GATACCACATTTGGTAATCGCAACATACATTTGACCCAAAAAAATGGTAAGTCAATTAATTTTCTCCACGCTA
ATCTATGATAACCCTATAAAACATGTCTTCCTCATTAGTTTAGTTAACTAGAAAGATGACCCAACTCTCTAAA
TACACTAAATCCAAAGTGTTGCACAACCGAATTCCAAATCAGTCATAAGTATGAATGACTAACAAGTTAATAT
AGACACATCATTCATAAACAGGGAGTAAGAGAGCGTAAATTAGTCTAAGTAAGAACTCAGTAGAATCTAAAAA
GGATCCTATTCCAAACGAACCTCATAAACGGGCTGACCATCAACCACTACCCAGGGAACGTACTGATGAGGAG
GCTGAAGTGGGCTCGTTTCTGCACCATACTTCAACTCAAGCTGCAGCAAATGGAAACGATTAGTGAGGAATGC
AACGGAAGCTTCCGCTTCCGAACAAGAACATAGTACATAAAGAGAAGGACACTAAGTACCTTGTCTCCATGTC
CACTGCTGAGGCAATCGGAAACAGGTTTAGAGTTGAGATTGAGCTTCTGATAACAAGTCTCCCACTTGTCGTA
CTTGTGCTCAGTCACCAAACTCTCAACACAGTGGATAAACGGGAAATGATCGCTCTACAAAATAAAAATGTAA
CGATCTCACACTAACTACGCTTCACCAAACAAAAAGATCACAATCAAATCTCATCATCCTACTTACCAATTTA
GGCCACGCATCAATCGCACAAGCTTCAACTGTATCCAAAAGGCATTCAAACGCACCGTGCTGCAACAAATTAG
CAACAATGTTTAACGTAATCTCGCTACAAGCATGCATGATAACGAAACGAGATCTTAGATACAAACAACATCT
TAAATAAATTTAATCAAATTATCGACAATGTTTAATGTAATCGCTACAATCATGCATGATGACGAAACGAGAT
CTCAGATTCAAACAACACCACAATACAAATTGAAGCTCTAATTTAATCAAATCAGGATACATCGGAAAGGTGT
GAGAACACCTGGCAAACGGCAGTGACATTATCGGACCGGACCTTGGTGTTACCCCACGGAGATAGATGGAGAT
CGACGATTGATATGAGATCGTCTTCGAAGACCTTCGTGAGGTGGTTAACGATGAACGAAGAACAGTACGGACA
TAGAGACTCGTAGTACAGTCCCAGCGACACTTTCGGAGAAGATGGCAGGTCAGATGATGATGACGATGATGAT
ACGAAGAAGATCAGAGAAACGTAGCAGAATAGGAGAAGAAGAAGCTTGCTCGTCGAAATCGACGCCATGATTG
CAAAGAGAAGCAACCTCTGTTGTATCGTCTTCGTCCTCTTCTCTTAATAACACGCATCTCGATATGCTCGGTG
CGAAACAGATGACAATAACCGATAAGGCCCGTCTCATTCTTTGTGTGGCCTTGTTCAAAGCCTAAATACTAA
TTATAAAATTTCATAAAAGCCCAAACGTTTATAACAAAGGCTCCGAATACTTAGTAAAATTTCTTTTGGACCA
AGTGCAAATATACATCAAATTAGCTACATTAATTTTTGGGTTAAGCAGTTGACCGAGAATTAAAGAGTGACAA
TATACATCAAAGCTTGGAATCAATCTCATACATGTGATGAACTAGAGGACCAATAAAATACTTGTCATGTCCA
TTGCTTAGGCAAACGAGGGACATGGATTATATAACCTCATGTATACAGATTATATATCAAATGAAAATTTTAG
GCTATTGGAGTACGTGAAGGATTTGATCAACAAGACTGAGACTGACGACGAGGTAAGCAAGTTGGGTACGATG
AATGTCGTCCCAGAAAAGGTAGTCGTTAGCGTCGGGACAAGTCCGAGTTAAAGGATTGCACAAGTATGATAGC
TCCAGCTCTCCTGTTCCGCAGCATCCTCTCGTTGTCTCCTTTATTCCTGTCCCTTTCGAAAAAATCGATTCAG
ACCACGAAAAAATGCACGGTATATGGCTATATAACAAACTGTAGACTCATAACCTGTAATGCGAGCACACTGG
ATTATAAACTCACCTTAGTTATTGTAAAATTAATCTTTCGACTTAATTATATGAAATGACGTCAACATAAAAA
TAGATATAATGAAAAATAATATGTATCATAGTGATTTGTGCTATTATCATCGATATCATCATGTTTAAACCAA
CAAATACATAGTTTTTTTTTAGCAAATACATATATTATTAACGAAAAAAAATTATATATAGTAATGTTTTAAT
TGTTGGATAGCCAACAAGTATAATACGTAAATTAGCAAATGCAAATGAGTTCTATATGCAGCCAAGCCACCT

DOWNY MILDEW RESISTANT CABBAGE AND BREEDING METHOD THEREFOR

CROSS-REFERENCE TO RELATED APPLICATIONS

The present application is based upon and claims the benefit of the priority from prior Japanese Patent Application No. 2017-173823, filed on Sep. 11, 2017; the entire contents of which are incorporated herein by reference.

TECHNICAL FIELD

The present invention relates to cabbage endowed with downy mildew resistance and a method for breeding the same. More specifically, the present invention relates to cabbage having a downy mildew resistant gene positioned in the vicinity of the loci represented by SEQ ID NO. 1 to SEQ ID NO. 7, and the method for breeding the same.

BACKGROUND ART

Downy mildew in Brassicaceae plants is a disease caused by *Hyaloperonospora brassicae*, which belongs to the oomycetes, and brings about damages on many crops such as *Brassica oleracea* species including cabbage, Brussels sprouts, cauliflower, broccoli, kohlrabi, *Brassica rapa* species including Chinese cabbage, turnip, and Komatsuna, and *Brassica napus* species including rapeseed.

The symptoms of this disease are mainly found in leaves; yellow to pale brown blotches with unclear borders are formed and gradually enlarged, and the leaves wither, whereby the growth is adversely influenced (FIG. 1). If the curds of broccoli and cauliflower, or the roots of turnip or Japanese radish are infected, brown or black discoloration occurs inside and outside the tissues, this greatly decreases their commercial values. Especially in a highly humid environment, the disease quickly spreads and causes a severe damage, so that chemical control with fungicides is usually carried out.

Cabbage (*B. oleracea* var. *capitata*), which is one of the most important crops of *Brassica oleracea*, has abundant varieties, and the varieties suitable to the domestic soils and climates are cultivated in many countries in the world.

However, even though cabbage has some lines that exhibit moderate resistance against downy mildew in an unknown heredity manner and likely due to quantitative factors, but the presence of downy mildew resistant varieties having single, dominant resistant factor is unknown.

Therefore, in the areas where downy mildew frequently occurs, disease control by fungicides must be carried out for reducing the disease, and this requires much labor and cost. Therefore, development of resistant breeding materials and resistant varieties have been desired.

However, in spite of such strong demands, downy mildew resistant varieties of cabbage have not been produced as far as the inventors know. The reason for this is likely that the genetic resources of cabbage include no useful downy mildew resistant factor.

Meanwhile, for broccoli (*B. oleracea* var. *italica*) which is a related species of cabbage, there are some reports on the heredity analysis of downy mildew resistant factors (for example, J. Amer Soc Hort Sci (2001), vol. 126, p. 727 (Non Patent Document 1), Euphytica (2002), vol. 128, p. 405 (Non Patent Document 2), and Euphytica (2003), vol. 131, p. 65 (Non Patent Document 3)).

However, these resistant factors in broccoli have not been used in breeding of cabbage. The reason for this is likely that the morphological characters of cabbage and broccoli are totally different. Broccoli can be hybridized with cabbage because both of them belong to *Brassica oleracea*, but broccoli has many characters which are unnecessary for cabbage, so that broccoli is very difficult to handle as a breeding material.

PRIOR ART LIST

Non Patent Document

Non Patent Document 1: M. Wang et al., J. Amer Soc Hort Sci (2001), vol. 126, pp. 727-, "*Inheritance of True Leaf Stage Downy Mildew Resistance in Broccoli*"

Non Patent Document 2: M. W. Farnham et al., Euphytica (2002) vol. 128, pp. 405-, "*A single dominant gene for downy mildew resistance in broccoli*".

Non Patent Document 3: P. S. Coelho et al., Euphytica (2003) vol. 131, pp. 65-, "*Inheritance of downy mildew resistance in mature broccoli plants*"

SUMMARY OF THE INVENTION

Problems to be Solved by the Invention

The present invention is intended to provide a novel cabbage having marked resistance against downy mildew, and a method for breeding the cabbage.

Means for Solving Problems

The inventors have developed markers linked to downy mildew resistant factors, and used them in the combination of broccoli and cabbage, and succeeded in breeding a cabbage line which has a downy mildew resistant factor and also has a high commercial value.

The *Brassica oleracea* plant obtained by hybridization of broccoli and cabbage by the inventors had a figure of a wild species in the original hybrid and the first backcross generation. Thereafter, the inventors repeated backcrossing for replacing the genome region irrelevant to downy mildew with the genotype of cabbage type through the selection of markers linked to downy mildew resistance and the application of genome-wide markers, thereby succeeding breeding cabbage which shows high resistance against downy mildew.

More specifically, the inventors have found a broccoli line which has downy mildew resistance applicable to a wide range of varieties, and developed markers linked to the downy mildew resistant factors held by the line, and proved that the use of them allows breeding a cabbage line with a high industrial value. The use of the downy mildew resistant cabbage or the method for breeding a downy mildew resistant cabbage provided by the present invention allows imparting downy mildew resistance to cabbage which has been susceptible to downy mildew.

The present invention is based on these findings.

More specifically, the present invention provides the following inventions.

<1> Cabbage or its progeny having resistance against downy mildew.

<2> The downy mildew resistant cabbage or its progeny according to <1>, having a downy mildew resistant gene which is positioned in the vicinity of the locus represented by any one or more of SEQ ID NO. 1 to SEQ ID NO. 7.

<3> The downy mildew resistant cabbage or its progeny according to <1> or <2>, having a downy mildew resistant gene which is detectable by any one or more of the primers having the nucleotide sequences represented by SEQ ID NO. 8 to SEQ ID NO. 21.

<4> The downy mildew resistant cabbage or its progeny according to any one of <1> to <3>, wherein the downy mildew is a disease caused by *Hyaloperonospora brassicae.*

<5> The downy mildew resistant cabbage or its progeny according to any one of <1> to <4>, wherein the downy mildew resistant gene is found in the broccoli variety specified by Accession Number FERM BP-22343.

<6> The downy mildew resistant cabbage or its progeny according to any one of <1> to <4>, wherein the downy mildew resistant gene is found in the cabbage variety specified by Accession Number FERM BP-22344.

<7> A portion of a plant body of the cabbage or its progeny according to any one of <1> to <6>.

<8> A seed of the cabbage or its progeny according to any one of <1> to <6>.

<9> First filial generation cabbage or its portion having resistance against downy mildew specified by Accession Number FERM BP-22344, or a seed of the cabbage.

<10> A method for breeding downy mildew resistant cabbage, including introducing downy mildew resistance from a *Brassica oleracea* plant having resistance against downy mildew into desired cabbage.

<11> A method for breeding downy mildew resistant cabbage, including introducing downy mildew resistance from a *Brassica oleracea* plant having resistance against downy mildew into desired cabbage, the downy mildew resistance being confirmed by a downy mildew resistant gene positioned in the vicinity of the locus represented by any one of SEQ ID NO. 1 to SEQ ID NO. 7.

<12> A method for breeding the downy mildew resistant cabbage according to <10> or <11>, wherein the *Brassica oleracea* plant having resistance against downy mildew is a *Brassica oleracea* plant other than cabbage.

<13> The breeding method according to any one of <10> to <12>, wherein the *Brassica oleracea* plant having resistance against downy mildew is a broccoli variety specified by Accession Number FERM BP-22343.

<14> The breeding method according to <10> or <11>, wherein the *Brassica oleracea* plant having resistance against downy mildew is a cabbage variety specified by Accession Number FERM BP-22344.

<15> The breeding method according to any one of <10> to <14>, wherein the introduction of downy mildew resistance into desired cabbage is achieved by continuous backcross of the cabbage.

<16> The breeding method according to any one of <10> to <15>, including assaying the presence of a downy mildew resistant gene using one or more of the DNA sequences represented by SEQ ID NO. 1 to SEQ ID NO. 7, or one or more of the primers or primer pairs which can amplify the DNA sequence.

<17> The breeding method according to <16>, wherein the primer is represented by any one or more of SEQ ID NO. 8 to SEQ ID NO. 21.

<18> The breeding method according to any one of <10> to <15>, comprising assaying the presence of a downy mildew resistant gene using any one or more of the primers having the nucleotide sequences represented by SEQ ID NO. 8 to SEQ ID NO. 21.

<19> A marker having any one of the nucleotide sequences represented by SEQ ID NO. 1 to SEQ ID NO. 7, the marker being able to detect a downy mildew resistant locus in a *Brassica oleracea* plant.

<20> A primer set including any one or more of the primers having the nucleotide sequences represented by SEQ ID NO. 8 to SEQ ID NO. 21, the primer set being able to detect a downy mildew resistant locus in a *Brassica oleracea* plant.

<21> A method for detecting downy mildew resistance in a *Brassica oleracea* plant, including using any one or more of markers having the nucleotide sequences represented by SEQ ID NO. 1 to SEQ ID NO. 7, or any one or more of the primers having the nucleotide sequences represented by SEQ ID NO. 8 to SEQ ID NO. 21.

Advantageous Effects of Invention

The downy mildew resistant cabbage of the present invention has marked resistance against downy mildew caused by *Hyaloperonospora brassicae*. Additionally, the use of the downy mildew resistant cabbage according to the present invention as a material allows further breeding a novel downy mildew resistant cabbage line. Furthermore, the use of a marker linked with downy mildew resistance according to the present invention allows detection or selection of downy mildew resistance even no inoculation test is carried out. The cultivation of a cabbage line bred according to the present invention allows cabbage cultivation even in areas where the cultivation has been difficult because of the occurrence of downy mildew, and reduces the labor and cost of chemical spraying which has been necessary in cultivation. Additionally, the downy mildew resistant cabbage according to the present invention allows shipping of fresh vegetables cultivated with a reduced number of chemical spraying, and further suppresses the occurrence of diseases, this allows harvest of fresh vegetables with a high excellent product rate.

BRIEF DESCRIPTION OF DRAWINGS

FIG. 8-1 illustrates the nucleotide sequences of the markers (DMTLR-1 to DMTLR-7).

FIG. 8-2 illustrates the nucleotide sequences of the markers (DMTLR-1 to DMTLR-7).

FIG. 8-3 illustrates the nucleotide sequences of the markers (DMTLR-1 to DMTLR-7).

FIG. 8-4 illustrates the nucleotide sequences of the markers (DMTLR-1 to DMTLR-7).

FIG. 8-5 illustrates the nucleotide sequences of the markers (DMTLR-1 to DMTLR-7).

EMBODIMENTS FOR CARRYING OUT THE INVENTION

Figure 1:
FIG. 1 illustrates a symptom by a downy mildew inoculation test (the left illustrates a susceptible line, and the right illustrates resistance line). In the figure, for the left susceptible line, formation of yellow to brown lesions is observed on the surface of leaves.

The present invention is described below in detail.

Downy Mildew Resistant Cabbage

The present invention relates to, as described above, cabbage having resistance against downy mildew (downy mildew resistant cabbage), or its progeny.

In the present description, "progeny" includes hybrids obtained by hybridizing the downy mildew resistant cabbage according to the present invention and a *Brassica oleracea* plant which can be hybridized with the plant. Accordingly, "progeny" also includes, for example, those obtained by hybridizing the downy mildew resistant cabbage according to the present invention as a pollen parent (male parent) and a *Brassica oleracea* plant as a seed parent (female parent) which can be hybridized with the plant. Additionally, "progeny" also includes, for example, the plants obtained by cell fusion of the downy mildew resistant cabbage according to the present invention and a plant which can be fused with the cabbage, and interspecific hybrid plants.

The term "*Brassica oleracea* plant" means a cruciferous plant, which is a *Brassica oleracea* plant belonging to genus *Brassica*, and includes, for example, *B. oleracea* var. *capitata* (cabbage), *B. oleracea* var. *italica* (broccoli), *B. oleracea* var. *botrytis* (cauliflower), *B. oleracea* var. *gemmifera* (brussels sprout), *B. oleracea* var. *gongyloides* (kohlrabi), *B. oleracea* var. *acephara* (ornamental cabbage, kale), and *B. oleracea* var. *albograbra* (Chinese kale).

The "cabbage" herein means a plant species belonging to *Brassica oleracea*, and is a plant species classified as *B. oleracea* var. *capitata.*

In the present description, "downy mildew" means a disease caused by an oomycete of the family Peronosporaceae, preferably a disease caused by *Hyaloperonospora brassicae*. Accordingly, resistance against downy mildew herein means resistance against the diseases caused by these pathogens.

Accordingly, the downy mildew resistant cabbage according to the present invention shows resistance against downy mildew fungus (preferably *Hyaloperonospora brassicae*), and gives single, dominant expression. The use of this plant as a material allows breeding a novel cabbage parental line having downy mildew resistance.

The "parental line" herein means a line bred for producing a hybrid variety and usually a hybrid variety is produced by hybridizing two or more parental lines having different phenotypes.

Accordingly, the "downy mildew resistance" in the present invention means resistance against a downy mildew pathogen *Hyaloperonospora brassicae*, and is more specifically based on the factor positioned in the vicinity of SEQ ID NO. 1 to SEQ ID NO. 7.

That is, according to a preferred embodiment of the present invention, the downy mildew resistant cabbage or its progeny according to the present invention has a downy mildew resistant gene positioned in the vicinity of the locus represented by any one or more of SEQ ID NO. 1 to SEQ ID NO. 7.

Here, the definition "represented by any one or more of SEQ ID NO. 1 to SEQ ID NO. 7" includes the case where the nucleotide sequences represented by SEQ ID NO. 1 to SEQ ID NO. 7 are within the range of certain sequence identity, or of the range having partial mutation. The sequences of the range which can be handled equally to those of SEQ ID NO. 1 to SEQ ID NO. 7 can be easily understood by those skilled in the art.

Accordingly, for example, the definition "represented by any one or more of SEQ ID NO. 1 to SEQ ID NO. 7" is used in the sense of including the case represented by any one or more of the following nucleotide sequences (a) to (c):

(a) any one or more of the nucleotide sequences represented by SEQ ID NO. 1 to SEQ ID NO. 7.

(b) any one or more of the nucleotide sequence having sequence identity of 95% or more to the nucleotide sequences represented by SEQ ID NO. 1 to SEQ ID NO. 7, and (c) any one or more nucleotide sequences prepared by deletion, substitution, insertion, and/or addition of one or a plurality of the nucleotide sequences represented by SEQ ID NO. 1 to SEQ ID NO. 7.

Therefore, according to a preferred embodiment of the present invention, the downy mildew resistant cabbage or its progeny according to the present invention is regarded as having a downy mildew resistant gene positioned in the vicinity of the locus represented by any one or more of the nucleotide sequences represented by the above-described (a) to (c).

In the (b), "having sequence identity of 95% or more to the nucleotide sequences represented by SEQ ID NO. 1 to SEQ ID NO. 7" includes SEQ ID numbers having sequence identity of at least 95%, preferably at least 96%, even more preferably at least 97%, yet even more preferably 98%, and particularly preferably at least 99% to the nucleotide sequences represented by SEQ ID NO. 1 to SEQ ID NO. 7 as calculated by using a known algorithm for homology search such as BLAST and FASTA (for example, using a parameter of default, or initial setting).

The term "sequence identity" herein means, for example, the percentage (%) of the number of identical nucleotides to the total number of the nucleotides including gaps, when two base (nucleotide) sequences are aligned (where a gap may be introduced or not introduced).

In the (c), "a plurality of" in "deletion, substitution, insertion, and/or addition of one or a plurality of the nucleotide sequences represented by SEQ ID NO. 1 to SEQ ID NO. 7" is, for example, about 10, preferably eight, more preferably six, even more preferably five, yet even more preferably four, further yet even more preferably three, and further yet even more preferably two, and particularly preferably one.

According to a preferred embodiment of the present invention, SEQ ID NO. 1 to SEQ ID NO. 7 may be SEQ ID NO. 22 to 28, respectively. SEQ ID NO. 22 to 28 include the sequences outside the sequences of SEQ ID NO. 1 to 7 between primers (including the sequences of the primers), and were discovered by the inventors in the below-described Example 2.

Accordingly, the phrase "represented by any one or more of SEQ ID NO. 22 to 28" means that only the parts of SEQ ID NO. 1 to 7 included in these sequences include that represented by any one or more of the above-described nucleotide sequences (a) to (c), and the case in which SEQ ID NO. 22 to 28 are represented by any one or more of the following nucleotide sequences (a') to (c').

(a') any one or more of the nucleotide sequences represented by SEQ ID NO. 22 to SEQ ID NO. 28, (b') any one or more of the nucleotide sequences having sequence identity of 95% or more to the nucleotide sequences represented by SEQ ID NO. 22 to SEQ ID NO. 28, and (c') any one or more of the nucleotide sequences prepared by deletion, substitution, insertion, and/or addition of one or a plurality of the nucleotide sequences represented by SEQ ID NO. 22 to SEQ ID NO. 28.

In the (b'), "having sequence identity of 95% or more to the nucleotide sequences represented by SEQ ID NO. 22 to SEQ ID NO. 28" includes SEQ ID numbers having sequence identity of at least 95%, preferably at least 96%, even more preferably at least 97%, yet even more preferably 98%, and particularly preferably at least 99% to the nucleotide sequences represented by SEQ ID NO. 22 to SEQ ID NO. 28 as calculated by using a known algorithm for homology search such as BLAST and FASTA (for example, using a parameter of default, or initial setting).

In the (c'), "a plurality of" in "deletion, substitution, insertion, and/or addition of one or a plurality of the nucleotide sequences represented by SEQ ID NO. 22 to SEQ ID NO. 28" is, for example, about 10, preferably eight, more preferably six, even more preferably five, yet even more preferably four, further yet even more preferably three, and further yet even more preferably two, and particularly preferably one.

For the "vicinity" referred to in the present invention, the degree of the distance can be easily understood by those skilled in the art from the relationship between the position of the marker and downy mildew resistant genes, and ordinary acquaintance of those skilled in the art. For example, depending on analysis conditions, it may be a distance of about 10 cM or less (for example, 7 cM).

Additionally, by using the nucleotide sequence represented by SEQ ID NO. 1 to SEQ ID NO. 7 as markers, the presence of a downy mildew resistant gene positioned in the vicinity of them can be estimated or confirmed from the loci represented by these sequences.

Accordingly, another embodiment of the invention provides a marker which can detect a downy mildew resistant locus in a *Brassica oleracea* plant, the marker having any one of the nucleotide sequences represented by SEQ ID NO. 1 to SEQ ID NO. 7.

Also provided is a method for detecting downy mildew resistance in a *Brassica oleracea* plant, including detecting the presence of a downy mildew resistant gene by using a marker of any one or more of the DNA sequences represented by SEQ ID NO. 1 to SEQ ID NO. 7.

The "any one of the nucleotide sequences represented by SEQ ID NO. 1 to SEQ ID NO. 7" may include any one of the nucleotide sequences represented by the above-described (a) to (c), as long as a downy mildew resistant gene can be specified.

The detection of these markers can be performed according to a method known to those skilled in the art, such as the PCR method, real time PCR method, RFLP method, LAMP method, or SNPs genotyping chip method.

As described above, the use of these markers and the detection method allows confirmation whether the object is "a downy mildew resistant cabbage or its progeny having a downy mildew resistant gene positioned in the vicinity of the locus represented by any one or more of SEQ ID NO. 1 to SEQ ID NO. 7".

A preferred embodiment of the present invention includes a downy mildew resistant gene which can be detected by one or more primers or primer pairs which can amplify the DNA sequences represented by SEQ ID NO. 1 to SEQ ID NO. 7.

According to a more preferred embodiment of the present invention, the downy mildew resistant cabbage or its progeny according to the present invention has a downy mildew resistant gene which can be detected by any one or more of the primers having the nucleotide sequences represented by SEQ ID NO. 8 to SEQ ID NO. 21. These primers may be hereinafter referred to as "DMTLR markers".

Here, when a DNA marker "has" a nucleotide sequence, it means that the marker has the nucleotide sequence. For the DNA marker in the present invention, any one or several (for example, one, two or three, preferably one or two, more preferably one) of the nucleotides within the corresponding nucleotide sequence may be substituted, deleted, added, or deleted, or, the sequence may include a portion of the corresponding nucleotide sequence and have certain properties. In these cases, the word "has" may be replaced with "includes". Additionally, when the substitution, deletion, addition, or deletion of one nucleotide is acceptable, "has" may be replaced with "substantially includes".

The downy mildew resistance herein can be detected and confirmed by carrying out PCR by using the primers represented by the nucleotide sequences 8 to 21.

Another embodiment of the invention provides a primer set which can detect a downy mildew resistant locus in a *Brassica oleracea* plant, the primer set including any one or more of the primes having the nucleotide sequences represented by SEQ ID NO. 8 to SEQ ID NO. 21.

Another embodiment of the invention provides a method for detecting downy mildew resistance in a *Brassica oleracea* plant, including using any one or more of the markers having the nucleotide sequences represented by SEQ ID NO. 1 to SEQ ID NO. 7, or any one or more of the primers having the nucleotide sequences represented by SEQ ID NO. 8 to SEQ ID NO. 21.

The use of these DNA markers allows efficient breeding a novel cabbage line having downy mildew resistance, without selection by an inoculation test.

The downy mildew resistant cabbage according to the present invention has the following characteristics.

(1) Specifically, it is a plant having any of the DNA sequences represented by SEQ ID NO. 1 to SEQ ID NO. 7 in the vicinity of a downy mildew resistant locus, and shows downy mildew resistance owing to the inclusion of the allele.

(2) The use of a line having the above-described sequence as a hybridizing material allows breeding a novel cabbage parental line having downy mildew resistance. The introduction of downy mildew resistance can be confirmed by an inoculation test. Alternatively, new markers may be designed from the DNA markers made based on SEQ ID NO. 1 to SEQ ID NO. 7, and the DNA sequences positioned in the vicinity of the SEQ ID NO. 1 to SEQ ID NO. 7 based on official information, and used for the selection of resistant plants. Furthermore, the use of markers in the vicinity of a downy mildew resistant locus also allows selection of individuals from which the non-target character linked to the downy mildew resistant locus has been separated.

(3) The cabbage of the present invention thus developed has resistance against a downy mildew pathogen, *Hyalop-*

*eronospora brassicae*, and thus allows reduction of labor and cost of fungicide spraying for disease control during the cultivation period.

According to a preferred embodiment of the present invention, the downy mildew resistant cabbage or its progeny according to the present invention may be any of the followings:

1) a downy mildew resistant cabbage or its progeny, where a downy mildew resistant gene is found in a broccoli variety specified by Accession Number FERM BP-22343;

2) a downy mildew resistant cabbage or its progeny, where a downy mildew resistant gene is found in a cabbage variety specified by Accession Number FERM BP-22344; and 3) a first filial generation cabbage having resistance against downy mildew, which is specified by Accession Number FERM BP-22344.

Here, the downy mildew resistant gene is "found" means that the gene existing in the specific variety is included in downy mildew resistant cabbage or its progeny. More specifically, the downy mildew resistant cabbage or its progeny having a downy mildew resistant gene found in the broccoli variety specified by Accession Number FERM BP-22343 includes the broccoli variety specified by Accession Number FERM BP-22343 and any one as long as they have the downy mildew resistant gene found in the broccoli variety specified by Accession Number FERM BP-22343.

According to another embodiment of the invention, the present invention also relates to a portion of the plant body of the downy mildew resistant cabbage or its progeny according to the present invention, or seeds of them.

The "a portion of the plant body" includes organs such as flower, leaf, stem, and root, or a part or tissues of them, or cells or cell aggregates from these organs or tissues.

Method for Breeding Downy Mildew Resistant Cabbage

The method for breeding the downy mildew resistant cabbage according to the present invention includes, as described above, introducing downy mildew resistance from a *Brassica oleracea* plant having resistance against downy mildew into desired cabbage.

The "*Brassica oleracea* plant having resistance against downy mildew" means a *Brassica oleracea* plant which has ability to restrict the growth and development of downy mildew pathogen (preferably *Hyaloperonospora brassicae*) or the damage it causes, and can be obtained by, for example, carrying out an inoculation test using the provided downy mildew pathogen (preferably *Hyaloperonospora brassicae*), and judging whether the plant has resistance against it. More preferably, in this inoculation test, the resistant factor held by the plant is a *Brassica oleracea* plant showing single dominant expression. More specifically, for example, an inoculation test is carried out according to the below-described Example 1, and this allows confirmation whether the object is "a *Brassica oleracea* plant having resistance against downy mildew" which can be used in the breeding method of the present invention.

Preferably, the "*Brassica oleracea* plant having resistance against downy mildew" is a *Brassica oleracea* plant other than cabbage.

More preferably, the "*Brassica oleracea* plant having resistance against downy mildew" is a broccoli variety specified by Accession Number FERM BP-22343, or a cabbage variety specified by Accession Number FERM BP-22344.

In the breeding method of the present invention, "introducing downy mildew resistance into desired cabbage" means introducing the factor of downy mildew resistance" of the "*Brassica oleracea* plant having resistance against downy mildew" into desired cabbage so as to impart downy mildew resistance to the cabbage.

The "desired cabbage" means cabbage which has no downy mildew resistance, and cabbage which can be hybridized with a "*Brassica oleracea* plant having resistance against downy mildew" and wants the introduction of downy mildew resistance. This cabbage has a useful character as cabbage.

The "downy mildew resistance" referred to herein can be confirmed by a known means such as an inoculation test of downy mildew, more specifically, a downy mildew resistant gene positioned in the vicinity of the locus represented by any one or more of SEQ ID NO. 1 to SEQ ID NO. 7.

The introduction of downy mildew resistance means the introduction of a gene which can express downy mildew resistance into desired cabbage. In the present invention, typically, this introduction can be achieved. The "*Brassica oleracea* plant having resistance against downy mildew" and the desired cabbage, selecting that having desired downy mildew resistance from the hybrid progenies thus obtained, and carrying out backcrossing using the cabbage as the backcross parent.

The means of confirming downy mildew resistance in the hybrid progeny after hybridizing may be an inoculation test of downy mildew (for example, Example 1 may be referred to), or the selection of a resistant plant may use the DNA markers made based on SEQ ID NO. 1 to SEQ ID NO. 7, and the markers newly designed from the DNA sequences positioned in the vicinity of the SEQ ID NO. 1 to SEQ ID NO. 7, which are selected based on official information. These markers include the marker having any one of the nucleotide sequences represented by SEQ ID NO. 1 to SEQ ID NO. 7 and the primers having the nucleotide sequences represented by SEQ ID NO. 8 to SEQ ID NO. 21. These confirmation means may be used in the process of backcross in the same manner, thereby selecting the progeny of downy mildew resistance.

According to a preferred embodiment of the present invention, the breeding method of the present invention includes the assay of the presence of a downy mildew resistant gene using any one or more of the markers of the DNA sequences represented by SEQ ID NO. 1 to SEQ ID NO. 7, or one or more of the primers or primer pairs which can amplify the DNA sequences. Yet more preferably, the primers are represented by any one or more of SEQ ID NO. 8 to SEQ ID NO. 21.

According to a preferred embodiment of the present invention, the breeding method of the present invention is carried out by introducing downy mildew resistance into desired cabbage by continuous backcross of the cabbage. More specifically, the breeding method of the present invention includes hybridizing a *Brassica oleracea* plant having resistance against downy mildew and desired cabbage, selecting a hybrid progeny having downy mildew resistance, and continuous backcrossing it by using the desired cabbage as backcross parent.

When backcross is carried out, generally, the number of backcrossing is preferably about five to seven.

When efficient backcross is carried out, a genome-wide DNA marker may be used to bring the object close to the backcross parent in the early stage.

For example, the first backcross generation (BC1F1) is a segregated generation, the genome substitutional rates of these individuals are different, and the enlargement of the size of the population allows the acquisition of individuals in which 90% or more of the genome region shows the same genotype as the backcross parent. The selection of these individuals allows conformance of the region other than the downy mildew resistant locus to the same genotype as the backcross parent with a few number of generations.

As a specific means useful as a genome-wide DNA marker, when the genome sequence information of the backcross parent is available, the DNA markers based on the information may be made for genotyping each locus.

Even when there is no genome sequence information of the backcross parent, the individual having a genotype close to that of the backcross parent can be selected from the segregated generation using random PCR method such as RAPD (random amplified polymorphic DNA), SRAP (sequence-related amplified polymorphism), or AFLP (amplified fragment length polymorphism). Alternatively, if SNPs genotyping chips (for example, the products of Affymetrix or Illumina), which are designed for exhaustively analyzing many SNPs scattered in a genome, are available, such means may be used for the analysis.

The downy mildew resistant line thus bred can be used not only as a direct variety, but also as parents or one parent in an F1 seed producing system.

Accordingly, another embodiment of the invention also provides a method of producing a F1 line using the downy mildew resistant line, which is obtained by the breeding method of the present invention, as the line of parents or one parent, and a method for producing the seeds of the F1 line.

EXAMPLES

The present invention is specifically described below with reference to the following examples, but the present invention will not be limited by these examples.

Example 1

By using genetic resources of broccoli held by Sakata Seed Corporation as materials, two lines of broccoli ("BR-23" and "BR-35") that show resistance against both of two downy mildew isolates (isolates Dm-A and Dm-B (where the isolate Dm-B has a wider spectrum of virulence to different varieties than Dm-A)) were found.

In order to identify the downy mildew resistant locus held by these resistant lines, firstly, by using the "BR-23" line as the material, the two lines ("BR-4" and "BR-24") showing susceptibility to the above-described two isolates were hybridized, thus making the F2 population and the BC1F1 population shown in Table 1.

As the indication of generation, F1 means the first filial generation, and BC1 means the generation subjected to backcross once. More specifically, "BC1F1" means the generation subjected to backcross once after passing the stage of the first filial generation.

These populations thus obtained were subjected to an inoculation test using an isolate with a wider spectrum of virulence, Dm-B.

In the inoculation test, the degree of occurrence of disease (disease severity) was evaluated for the first to third true leaves of each individual according to the following disease severity score:

0: no symptom,

1: brown blotches are formed, no spore formation,

2: slight spore formation on brown blotches,

3: moderate spore formation, and

4: a large amount of spore formation.

The result is as shown in Table 1.

As indicated by the result, in the F2 population, the ratio of resistance:susceptibility was 3:1, while in the BC1F1 hybridized with a susceptible line, the ratio was 1:1. These findings revealed that the present disease resistant factor works in a single dominant manner.

TABLE 1

Genetic analysis using broccoli "BR-23" (small population)

| Line | Generation | Expected value | Number of individuals | Disease severity 0 | 1 | 2 | 3 | 4 | mapping population |
|---|---|---|---|---|---|---|---|---|---|
| BR-23 | Resistant parent | R:S = 1:0 | 39 | | 29 | 10 | | | |
| BR-4 | Susceptible parent | R:S = 0:1 | 20 | | | | | 20 | |
| BR-24 | Susceptible parent | R:S = 0:1 | 20 | | | | | 20 | |
| (BR-23 × BR-4) self | F2 | R:S = 3:1 | 60 | | 3 | 35 | 1 | 21 | mapping population-1 |
| (BR-23 × BR-24) self | F2 | R:S = 3:1 | 65 | | 2 | 49 | 3 | 11 | mapping population-2 |
| BR-23 × (BR-23 × BR-4) | BC1F1 | R:S = 1:0 | 40 | | 16 | 24 | | | |
| BR-23 × (BR-23 × BR-24) | BC1F1 | R:S = 1:0 | 39 | | 7 | 32 | | | |
| (BR-23 × BR-4) × BR-4 | BC1F1 | R:S = 1:1 | 39 | | 3 | 19 | | 17 | mapping population-3 |
| BR-24 × (BR-23 × BR-24) | BC1F1 | R:S = 1:1 | 40 | | 1 | 19 | | 20 | mapping population-4 |

Example 2

In Table 1, by using the F2 population that showed segregation of resistance and susceptibility (the mapping population-1 and -2) and the BC1F1 population (the mapping population-3 and -4) as the materials, the RAPD markers were searched by the bulked segregant analysis method (BSA method).

As the RAPD primers, 1180 kinds of 10mer primers designed by Operon Technologies, Inc. and 460 kinds of 12mer primers designed by BEX Co., Ltd. were used.

As the bulk DNA, four resistant individuals and four susceptible individuals were selected from the mapping population-4, and their DNAs were used to make a bulk DNA of resistant individuals and a bulk DNA of susceptible individuals were made.

As the primary screening of the RAPD markers, the two kinds of bulk DNAs were subjected to RAPD (randomly amplified polymorphic DNA) by using 1640 kinds of primers, thereby selecting 245 kinds of markers that showed polymorphism.

In the secondary screening, two individuals that showed resistance and two individuals that showed susceptibility were selected from the mapping population-4, and used as templates to select 36 kinds of markers that showed the similar patterns to the polymorphism shown in the primary screening.

In the tertiary screening, four individuals that showed resistance and four individuals that showed susceptibility were selected from the mapping population-4, and used as templates to select 11 kinds of markers that showed the similar patterns to the polymorphism shown in the secondary screening.

In this state, those showed the almost same segregation pattern of the markers as the phenotype were applied to all the individuals of the mapping population-1 to the mapping population-4, and the degree of contradiction between these markers and the score of the phenotype was confirmed, and the markers having a strong correlation with the phenotype were selected.

In the above-described test, seven kinds of markers of the 11 kinds of markers which had been confirmed to be linked with the downy mildew resistant factor were analyzed for the nucleotide sequences of the amplified DNA fragments, and sequence-specific primers were designed, thus attempting conversion to SCAR (sequence characterized amplified region).

Firstly, the DNA fragments amplified by RAPD were cut out from an agarose gel, cloned, and then their nucleotide sequences were analyzed. As a result of this, the nucleotide sequences of the above-described seven kinds of markers (DMTLR-1 to DMTLR-7) were specified (SEQ ID NO. 1 to SEQ ID NO. 7, respectively) (FIG. 8). In the specification of the sequences, the sequences of SEQ ID NO. 22 to 28 were specified first, and these sequences had the sequences of SEQ ID NO. 1 to 7 sandwiched between SCAR primers (including the sequence of the SCAR primer). In FIG. 8, the sequence indicated with an underline is the SCAR primer, and the sequences sandwiched between SCAR primers (including the SCAR primer) correspond to SEQ ID NO. 1 to 7, respectively.

For the cloning, pBluescriptII SK(−) (obtained from Stratagene) was used as the vector, and JM109 (*E. coli* JM109, obtained from Toyobo Co., Ltd.) was used as the competent cell. The analysis of the nucleotide sequences used DNA sequencer ABI3130 (Applied Biosystems).

For the markers whose nucleotide sequences were decoded, in order to amplify the target sequences specifically, the primers (SEQ ID NO. 8 to 21) were designed by using "Primer 3" software (a design supporting software for polymerase chain reaction (PCR), open source software) (Table 2).

Figure 2:
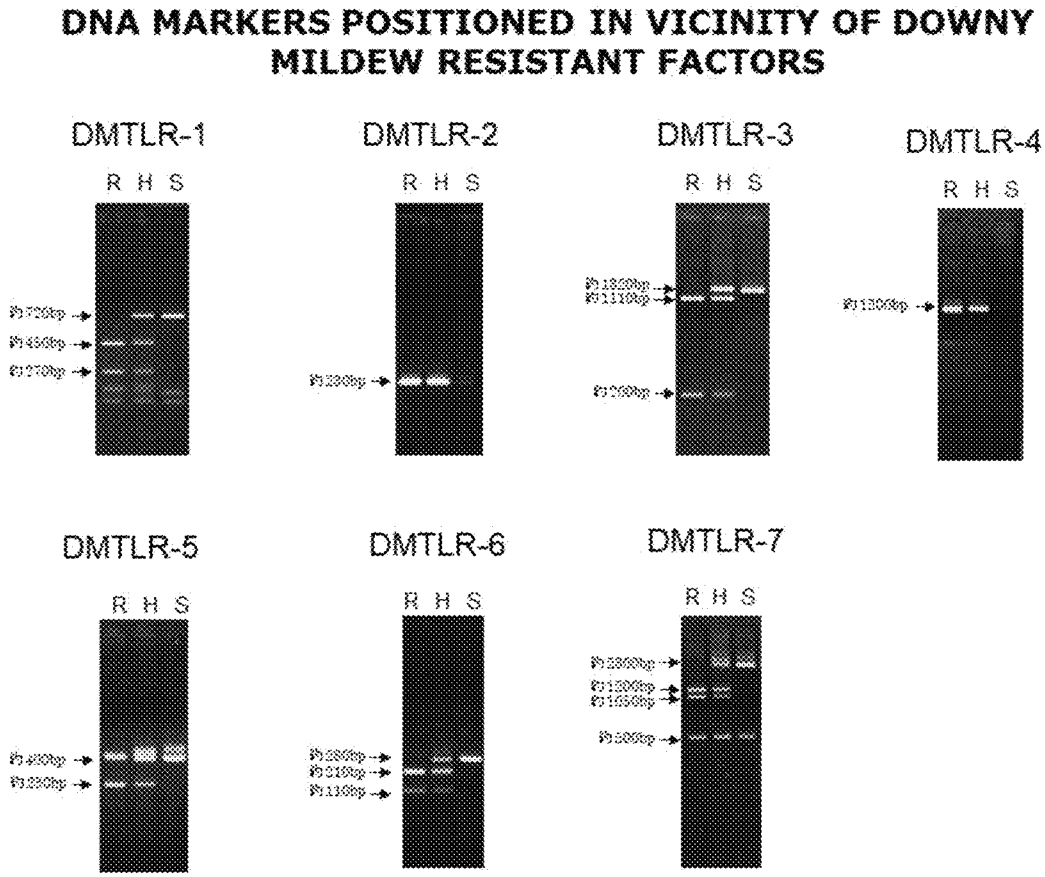
FIG. 2 illustrates an electrophoretic pattern of a DNA marker linked to the vicinity of a downy mildew resistant factor (Example 2).

Additionally, the results of the electrophoresis test on these primers (markers) (electrophoretic patterns) are shown in FIG. 2.

The markers thus developed are herein referred to as "DMTLR markers".

TABLE 2

| Marker Name | Sequence | PCR condition (annealing temperature/cycle) | Restriction enzyme | Marker type | Sequence No. |
|---|---|---|---|---|---|
| DMTLR-1-Fw | CGGTCTTAGTTGATTTCTCAAG | 55° C., 30cycle | TaqI | co-dominant | SEQ ID NO. 8 |
| DMTLR-1-Rv | GATCACCCTGTACTAGCAATC | | | | SEQ ID NO. 9 |
| DMTLR-2-Fw | AGTAGGGAGTAAACCAACGAG | 55° C., 30cycle | — | dominant | SEQ ID NO. 10 |
| DMTLR-2-Rv | CCACGAGTGCATATTAGGTTG | | | | SEQ ID NO. 11 |
| DMTLR-3-Fw | GTGCTCCGTCAAGATTCGAC | 55° C., 30cycle | XbaI | co-dominant | SEQ ID NO. 12 |
| DMTLR-3-Rv | GGACCTAATGAATGGAGAGCTAC | | | | SEQ ID NO. 13 |
| DMTLR-4-Fw | GCATGAGTAAGTCAAGCAACT | 55° C., 30cycle | — | dominant | SEQ ID NO. 14 |
| DMTLR-4-Rv | CAATGAGGTTGTGCTTTCCTG | | | | SEQ ID NO. 15 |
| DMTLR-5-Fw | CTCTGCAATATTGTCCTTGATG | 55° C., 30cycle | FokI | dominant | SEQ ID NO. 16 |
| DMTLR-5-Rv | GCAATTCAGTAGACCAAGCT | | | | SEQ ID NO. 17 |
| DMTLR-6-Fw | CGATCTCACACTAACTACGCT | 55° C., 30cycle | MboI | co-dominant | SEQ ID NO. 18 |
| DMTLR-6-Rv | AATCTGAGATCTCGTTTCGTCA | | | | SEQ ID NO. 19 |
| DMTLR-7-Fw | TTATAGAAGGCCTGTGTACGAC | 55° C., 30cycle | HpaI | co-dominant | SEQ ID NO. 20 |
| DMTLR-7-Rv | GTGGCTTGGCTGGATATAGAA | | | | SEQ ID NO. 21 |

Example 3

By using the same F2 population as the mapping population-2 used in Example 2, resistance reaction to the downy mildew isolate Dm-A was also examined.

The size of the F2 population was 240 individuals (the mapping population-5), and the reaction of the individuals to Dm-A was examined; the segregation as given in Table 3 was exhibited. The inoculation test on the isolate Dm-A was carried out and evaluated in the same manner as in the inoculation test of Example 1.

TABLE 3

| Genetic analysis using broccoli "BR-23" (large population) | | | | | | | | | |
|---|---|---|---|---|---|---|---|---|---|
| | | | Number of examined | Number of individuals by disease severity | | | | | |
| Line | Generation | Expected value | individuals | 0 | 1 | 2 | 3 | 4 | mapping population |
| BR-23 | Resistant parent | R:S = 1:0 | 15 | 11 | 4 | 0 | 0 | 0 | |
| BR-24 | Susceptible parent | R:S = 0:1 | 15 | 0 | 0 | 1 | 10 | 4 | |
| (BR-23 × BR-24) self | F2 | R:S = 3:1 | 240 | 123 | 54 | 3 | 52 | 8 | mapping population-5 |
| BR-24 × (BR-23 × BR-24) | BC1F1 | R:S = 1:1 | 165 | 70 | 15 | 8 | 66 | 6 | |

As a result of comparison with the genotype by the SCAR marker made in Example 2, high correlation with the phenotype was confirmed. As a result of this, the downy mildew resistant factor of the line "BR-23" was estimated to show resistant reaction against two isolates with a single gene.

On the basis of the analysis result above, the linkage relationship between the phenotypes in the population and the markers was analyzed by using "Mapmaker 2.0" (Whitehead Institute), which is a software for analyzing the linkage relationship of markers.

Figure 3:
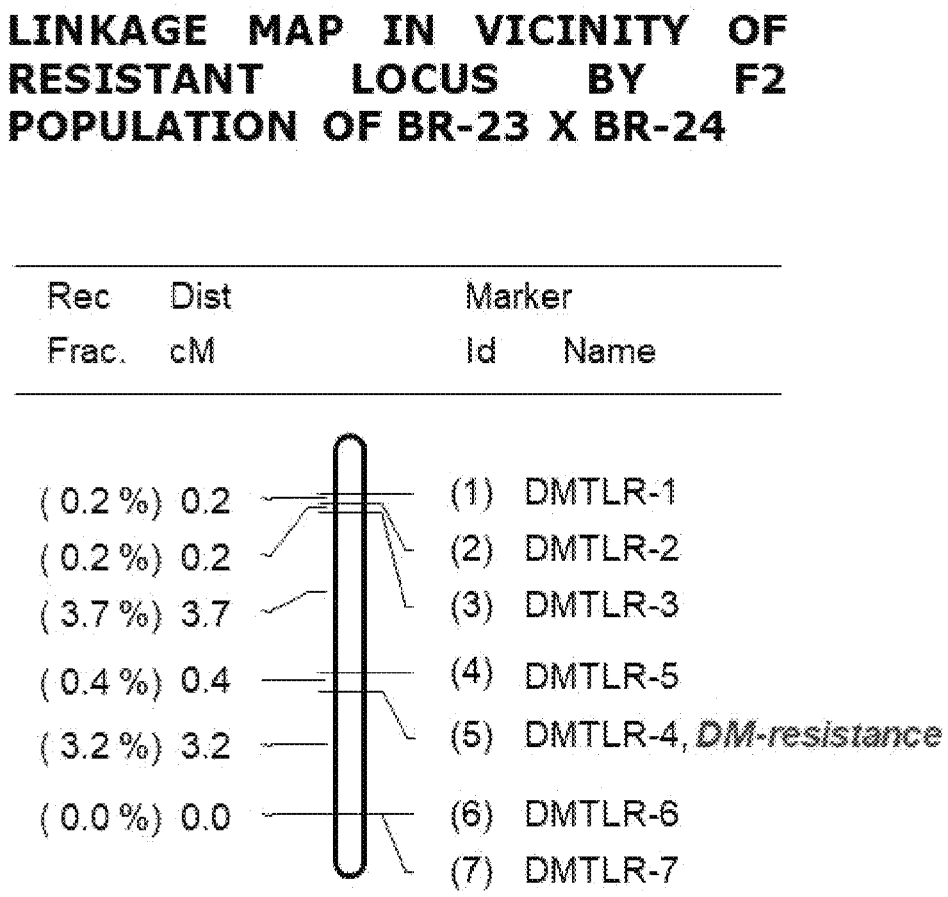
FIG. 3 illustrates a linkage map in the vicinity of a downy mildew resistant factor (Example 3).

The result is as shown in the linkage map of FIG. 3.

As indicated by the result, it was estimated that resistant factors are positioned in the vicinity of SEQ ID NO. 1 to 7, especially in the immediate vicinity of SEQ ID NO. 4 and SEQ ID NO. 5.

Example 4

For the line "BR-35" which is different from the resistant line "BR-23" analyzed in Example 2, in order to confirm whether it has the same resistant factor as the line "BR-23", an F2 segregated population with the susceptible line "BR-13" was made, and an inoculation test using the isolate Dm-A was carried out (Table 4). The inoculation test using the isolate Dm-A was carried out and evaluated in the same manner as the inoculation test in Example 1.

TABLE 4

| | | Number of | Number of individuals classified by disease severity score | | | | | |
|---|---|---|---|---|---|---|---|---|
| Variety, line | Generation | individuals | 0 | 1 | 2 | 3 | 4 | mapping population |
| BR-35 | Resistant parent | 12 | 5 | 7 | | | | |
| BR-13 | Susceptible parent | 12 | | | | 8 | 4 | |
| BR-35 × BR-13 | F1 | 12 | 1 | 9 | 2 | | | |
| (BR-35 × BR-13) F2 | F2 | 180 | 23 | 83 | 30 | 33 | 11 | mapping population-6 |

Furthermore, PCR was carried out by using SEQ ID NO. 8 and 9, the genotype of each individual was examined; all of the 42 individuals in which the locus exhibited resistant homozygous type and the 83 individuals showed heterozygous hetero type showed resistance (Table 5).

TABLE 5

| | | Number of | Number of individuals classified by disease severity score | | | | |
|---|---|---|---|---|---|---|---|
| Variety, line | Generation | individuals | 0 | 1 | 2 | 3 | 4 |
| Individual whose DMTLR-1 showed R homozygous in mapping population-6 | F2 | 42 | 10 | 28 | 4 | 0 | 0 |
| Individual whose DMTLR-1 showed heterozygous in mapping population-6 | F2 | 83 | 13 | 52 | 18 | 0 | 0 |
| Individual whose DMTLR-1 showed S homozygous in mapping population-6 | F2 | 55 | 0 | 3 | 8 | 33 | 11 |

Table 5 shows the result of classification of 180 individuals of mapping population-6 in Table 4 according to the genotype of the DNA marker DMTLR-1.

The polymorphism and phenotype showed by the markers had an extremely high correlation, so that the two kinds of broccoli downy mildew resistant lines "BR-23" and "BR-35" were estimated to have an identical resistant factor.

The downy mildew resistant gene held by "BR-35" can be found in the broccoli F1 variety "Sawayutaka", derived from "BR-35" as one parent.

The seeds of the broccoli F1 variety "Sawayutaka" are internationally deposited (originally deposited) in NITE-IPOD (Room 120, 2-5-8 Kazusakamatari, Kisarazu, Chiba) on Aug. 18, 2017 (index for identification attached by the depositor: SSC-BRO-17-001, Accession Number: FERM BP-22343).

Example 5

"BR-23" and "BR-35", which are the broccoli lines held by Sakata Seed Corporation, were used as materials having downy mildew resistance, line "CB-20", line "CB-35", line "CB-23", or line "CB-97" was selected from the four varieties (Yoshin, Kandama, spring, and ball types, respectively) as the cabbages to which the resistance is introduced, and used as the backcross parental lines in a hybridizing test.

For efficiently pursuing backcross (BC), basically, DNA assay using a developed DMTLR marker was carried out, individuals including the downy mildew resistant locus as heterozygous were selected, and the cabbage lines "CB-20", "CB-35", "CB-23", and "CB-97" were continuously backcrossed while their phenotypes were confirmed.

Firstly, the broccoli lines "BR-23" and "BR-35" were hybridized with the cabbage lines "CB-20", "CB-35", "CB-23", and "CB-97" to F1 seeds were produced, and the DNA selection with DMTLR markers and continuous backcross were carried out.

In order to efficiently carry out the backcross, selection using 20 kinds of RAPD primers were carried out, followed by selection of the individuals showing the genotypes close to "CB-20", "CB-35", "CB-23", and "CB-97", which are their backcross parental lines in their backcross lines.

As a result of this, the individuals whose RAPDs markers were completely coincident with their backcross parental lines were selected in the BC2F1 generation in "CB-20", and the BC3F1 generation in other "CB-35", "CB-23", and "CB-97".

In the BC2F1 generation or the BC3F1 generation, resistance and susceptibility were discriminated with a DMTLR marker, and each of these genotypes were prototyped together with their backcross parental lines in either or both of Kakegawa Research Center or Kimitsu Breeding Station of Sakata Seed Corporation.

The results are shown in Table 6 and FIGS. 4 to 7.

Table 6 shows the trial production result of the line made by introducing a downy mildew resistant factor into the cabbage line "CB-20" in the fields, and the evaluation result of disease severity of downy mildew. In the segregated generation during backcross, the individual which had been judged as having a downy mildew resistant factor by the DMTLR marker showed resistance even it was heterozygous, and the individual judged as having no downy mildew resistant factor showed susceptibility. Additionally, for the phenotype, the grass figure markedly close to that of the Yoshin type "CB-20" as the backcross parental line.

TABLE 6

| Line | DMTLR marker genotype | Number of individuals | Disease severity 0 | 1 | 2 | 3 | Average disease severity |
|---|---|---|---|---|---|---|---|
| CB-20 | S | 18 | | 3 | 3 | 12 | 2.5 |
| isogenic line (R) of CB-20 | R | 18 | | 17 | 1 | | 1.1 |
| isogenic line (S) of CB-20 | S | 17 | | | 5 | 12 | 2.7 |

Figure 4:
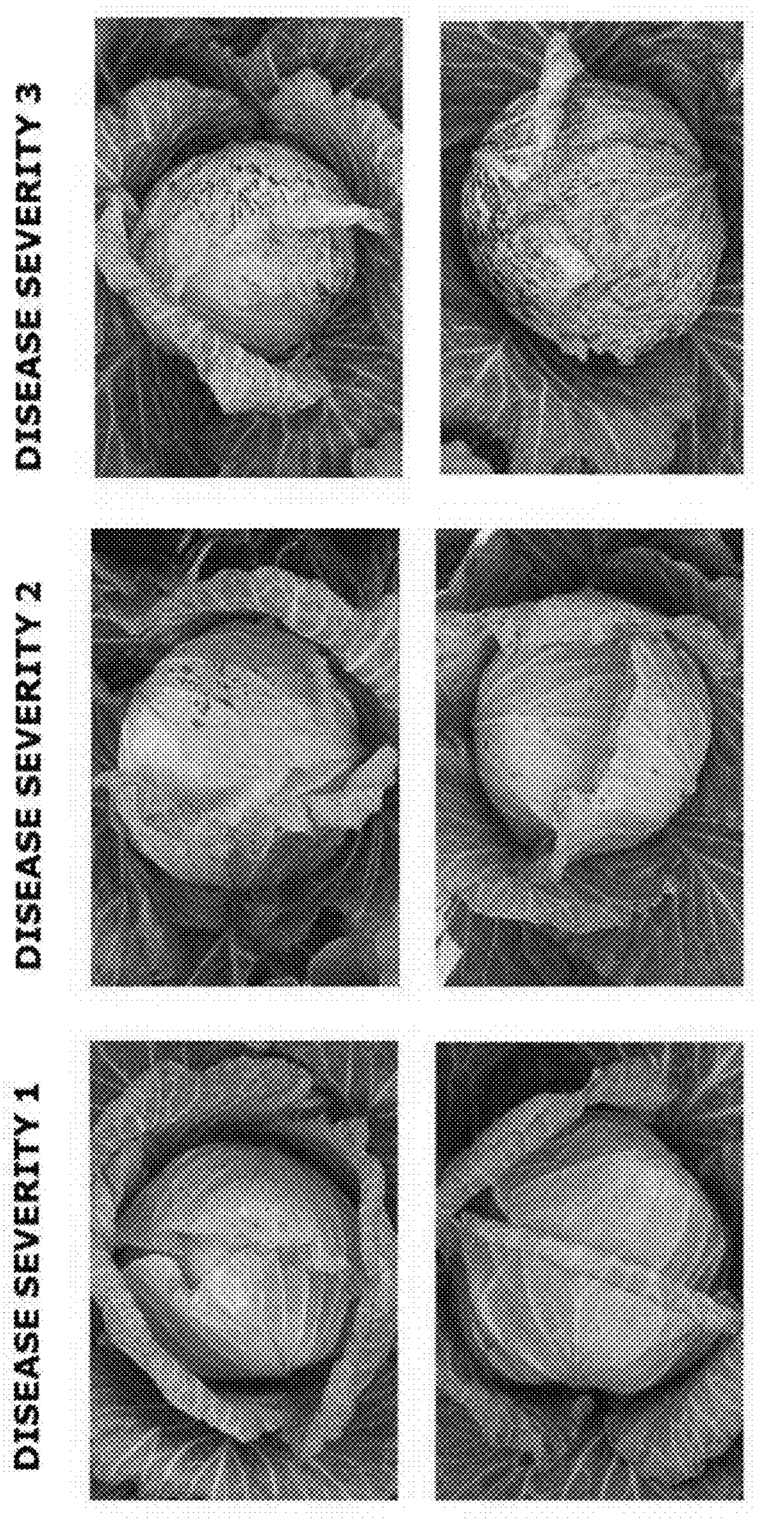
FIG. 4 illustrates an index of disease severity score in field trial production of Example 5.

The symptoms of the scores listed in Table 6 are given in FIG. 4. As the index of the disease severity score, the disease severity means the following condition.

Disease Severity

0: no symptom,

1: few number of lesions,

2: moderate number of lesions,

3: many lesions.

Figure 5:
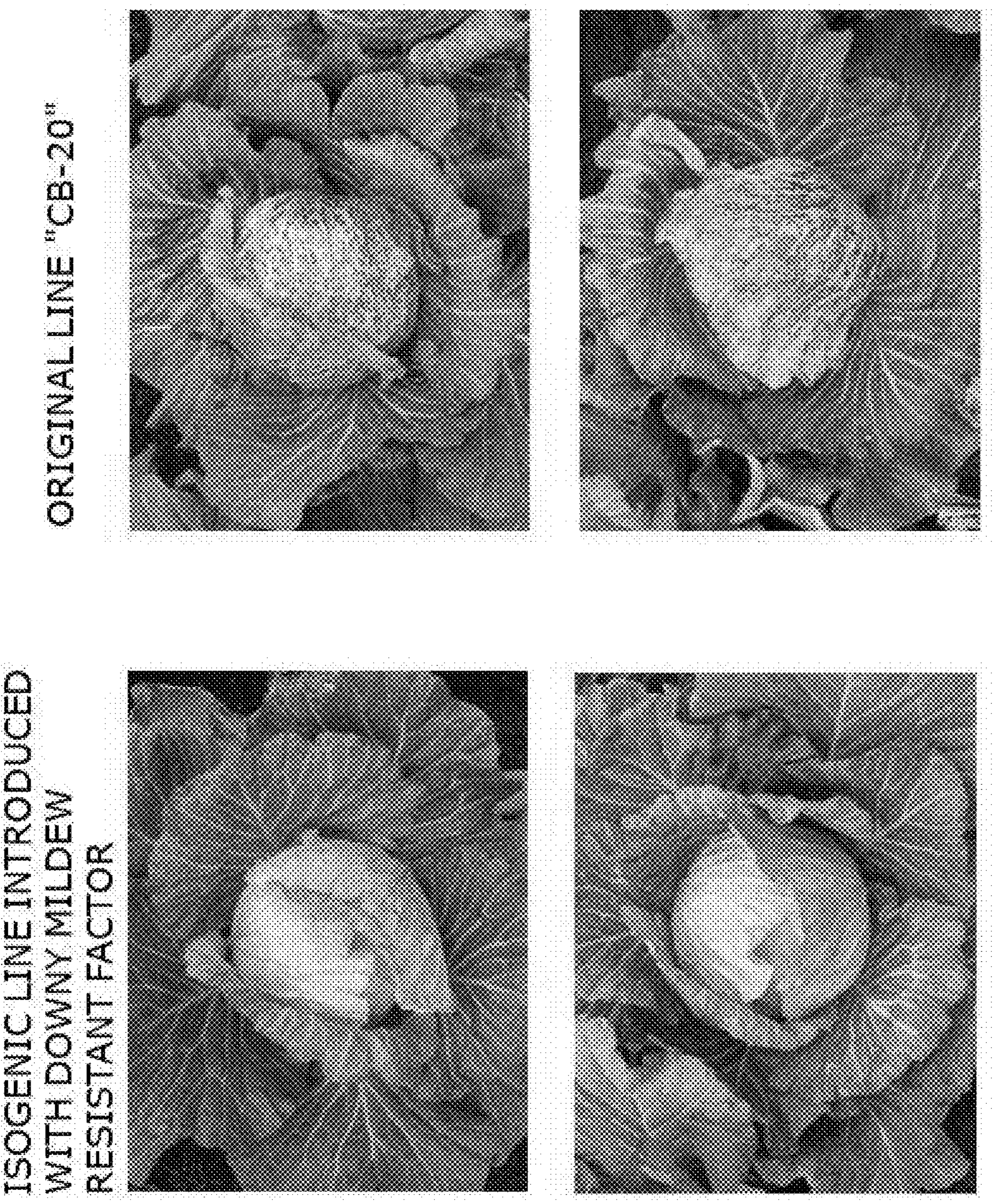
FIG. 5 illustrates the result of field trial production of a cabbage line bred according to the present invention (Example 5), including the condition of "CB-20" (original parental line) and the isogenic line introduced with a downy mildew resistant factor.

The photographs of "CB-20" (original parental line) shown in Table 6 and the isogenic line introduced with a downy mildew resistant factor were given in FIG. 5. As indicated by the figure, the isogenic line introduced with a downy mildew resistant factor suppressed the occurrence of downy mildew in comparison with the parental line "CB-20".

Furthermore, the lines backcrossed with three other cabbage lines "CB-35", "CB-23", and "CB-97" were also subjected to trial production investigation in the field.

Figure 6:
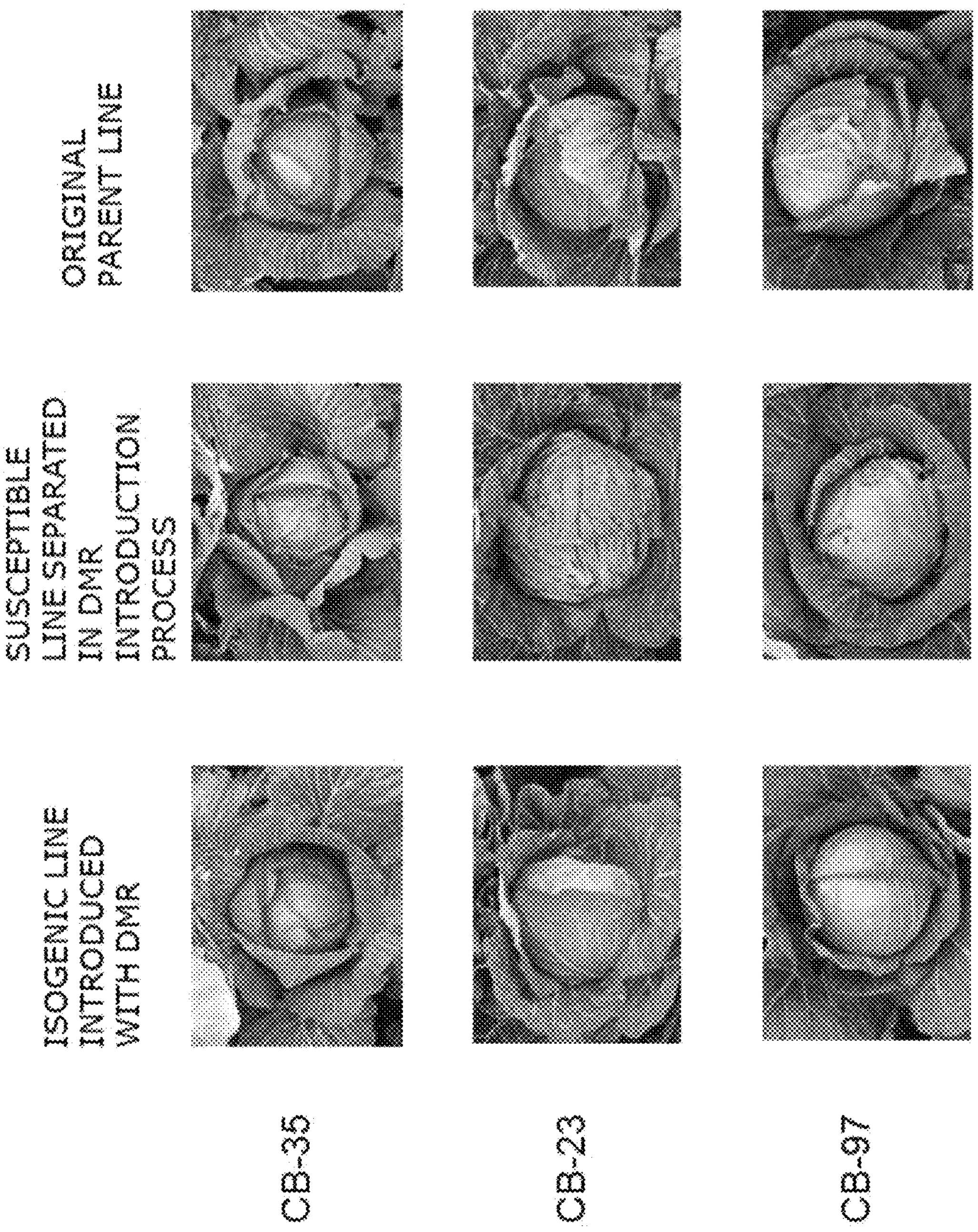
FIG. 6 illustrates the result of field trial production of three cabbage lines bred by the present invention (Example 5).

The result is as shown in FIG. 6.

As indicated by the result, the line introduced with a resistant locus expressed resistance in the main leaves and head even it was hetero, and was confirmed to be equivalent to the parental lines "CB-35", "CB-23", and "CB-97", which are Kandama, spring, and ball types, respectively. More specifically, as indicated by FIG. 6, the isogenic line introduced with a downy mildew resistant factor suppressed the occurrence of downy mildew in comparison with the original parental line.

Thereafter, the Yoshin type cabbage "CB-20", which is especially vulnerable to downy mildew, was subjected to several times of backcrossing, 20 individuals were selected from the lines cultivated in the field of Kakegawa Research Center, a homozygote with downy mildew resistance was obtained from anther and pollen culture, whereby first breeding a downy mildew resistant cabbage parental line having practical properties as the parent of a F1 variety was successfully achieved.

Example 6

Further, by using "DMR-CB-20" (the DM cabbage line bred as described above) with downy mildew resistance as the pollen parent, and the other promising cabbage line "CB-5" cytoplasm male sterile line as the seed parent, F1 (name of prototype variety: SK3-005) were produced.

The F1 line was continuously prototyped in Kimitsu Breeding Station of Sakata Seed Corporation, and stable expression of downy mildew resistance was confirmed.

The first breeding of the downy mildew resistant F1 cabbage variety was thus achieved.

The seeds produced from the bred downy mildew resistant F1 cabbage variety are internationally deposited (originally deposited) in NITE-IPOD (Room 120, 2-5-8 Kazusakamatari, Kisarazu, Chiba) on Aug. 18, 2017 (index for identification attached by the depositor: SSC-CAB-17-001, Accession Number: FERM BP-22344).

The original F1 variety (the F1 variety obtained by using the original parental line "CB-20") and the novel F1 variety introduced with downy mildew resistance (F1 variety having downy mildew resistance) was compared.

Figure 7:
FIG. 7 illustrates the result of trial production of the first filial generation (F1) variety using the cabbage parental line "DMR-CB-20" bred by the present invention (Example 6).
Figure 7:

The result is as shown in FIG. 7.

As indicated in FIG. 7, the F1 variety (left photograph) to which downy mildew resistance had been imparted suppressed the occurrence of downy mildew in comparison with the original F1 variety.

SEQUENCE LISTING

```
SEQUENCE LISTING
<110> Sakata Seed Corporation

<120> Cabbage having resistance to downy mildew and method for producing
the cabbage

<130> 800523JP01

<160>   28

<170> PatentIn version 3.5

<210>    1
<211> 1022
<212> DNA
<213> Unknown

<220>
<223> Marker 1

<400>    1
cggtccttag ttgatttctc aagtttgggt gtttgtccaa tcatctcttg gtacagttga      60
agcaaaagct tcatctctgc atataatact cagaacaatc aataatttta aaaagaaaac     120
aacagagtgc tataatgaga gagagagaga gagagagaga gactcactct cttgaatttc     180
gactgctgcc ttgcagtttc tgaagtcggg agctcgtagt acctatacaa ttaccagaac     240
atatactctc cgttgatatc taattaattc cacaaacaga gagaagagta gtggagattt     300
catacctcga gaacgtgagg gcgaagatcc ttgacaagga gacgcatctt gtagtagttg     360
gagttctcca ccttcagatt cccttccagc cccctctttc tccccttga cgacggatct     420
gacggagcca cctgagctcc tcctatatgt ggccgactcg gaaccggcgg gttatctaag     480
tccatcgccg gcgaagatct ctgatctgct gcagctgctg taggaagcgg gagagatgaa     540
gtagcggaag gaggaggagg agttgccgcg gaggtcgatt tctccatttt caaaaagggg     600
gttttctcaa ccgtaacacc ccagcacggg acgcagcagc cgggaactta aaacgaccgc     660
gttgtaagaa atctactgat tcggttaggg cctacttggg ggcccattat cttttttctt     720
tgtctaaacg gcccgtctgt atccgatgac catcatatag aagggtaaat catcaagtaa     780
caacaacact gcaacagaca agggacatat gtagctgaac agagaactct ctattcatta     840
gactgagata tatgttcata ataaattaag tcaaatcctg cataatagct caaagctgga     900
tttaatcatt cataattcca tgaatttttt ttacatagat atagtcttca gtttgacccc     960
aaaaaaaaaa aatagtcttc atatactcat ctctccaaag tgattgctag tacagggtga    1020
tc                                                                   1022

<210>    2
<211>  220
<212> DNA
<213> Unknown

<220>
<223> Marker 2

<400>    2
agtagggagt aaaccaacga gtgtaaatat cttccccaag ccgttccggg atgatgtgca      60
aggtaaacca agtgatggct atggggacaa ggaaagaaac aaaatgttcc tgcatgaaaa     120
tattgaagtt tgatgcaaac ccacaaattt ggtatatatt tcaaagttat tggttcgtgt     180
tcaaacgggt atatgctaac aacctaatat gcactcgtgg                          220

<210>    3
<211> 1314
<212> DNA
<213> Unknown

<220>
<223> Marker 3

<400>    3
gtgctccgtc aagattcgac gatcgtgttt tgtttccctt tttactttaa ctctcttcac      60
tcttcttcct tcattctcct cttctgatgg gaagccatag caacgcggag aaagatgaat     120
ccgccaccga gacggatgct acaacacggc agggatctct ctctgttaca gagtccaaca     180
ccgattgcga cgcagacgtc ttgcctcctc ctcctcctgc ggacgtgagt caattcgaag     240
aaggagagaa agttttagcc aaccacaaag gtcgtttcta cgaagccaag gtaatgttat     300
ttttgtctaa aattggaatg ttgtttgtgc ttttgtgttt aaaatttgat ctttgtttta     360
tgttttcagg ttcttgaaat tgcatttaaa gacaatgaat ggaactatta tgtgcattac     420
attgtaagtt tagattttat tttgttttgc gtaaccacga atctctgtaa aagcataaac     480
```

-continued

SEQUENCE LISTING

```
aaataaaaca catttattgt taatgctgcc gttattatat ttttgccgtt ttcaatatgt      540
aatcttttgt attttctttg gtttttacag ggttggaaca aaaggttagt agaccatccg      600
acagtactgt cacttactgc cggctttta ttgtctgaat aatctttctg tacattgcat      660
catcggtctg aataatcatt ctgctgctaa atcaaaacgt ttgccaagat tacaagtttt      720
ttttgtttct aatgcattga taatttcatg gtttgattat tgttgtatat ctttgtaatg      780
attagttatt tgtatggaca gttgggacga atggataggt catgattgtg tgttgaaaca      840
caccgaggag aatattaagg aacagggtat taagcaagga gtcaagagtg ctatggcttg      900
gagagtgtcc aaggtgaaac ctagatgccc taatggtcag tgttctgggt cttttattag      960
aggctttgtt gcatgcttta tagatcatat gctagatatt atcatcattc tcttgttaat     1020
atattttgca gttgctagag gaagaaagcg gaagcaagat tctgttgata cactagtctc     1080
tccaatggtg tggattttcc tttcattttt ctctagattc caagtttctt tctattgttt     1140
tctgatcagt ttttgcctga ttgtttttgt tgtttgctgg atacaggagg agaatttggt     1200
tgctacagac aacctttttaa ctttcaatat cccgtcagcg ttgaggaagc aactcatcga    1260
cgattatgaa ttcgttactc agatgcaaaa ggtagctctc gattcattag gtcc           1314

<210>    4
<211> 1300
<212> DNA
<213> Unknown

<220>
<223> Marker 4

<400>    4
gcatcactaa gtcaagcaac tttgatctct tggttttaag tttcaaagaa gctatctttg       60
gacgtggatt gtttgacaga agtatacatc tttggactaa gtctgataga actagtagag      120
aacctcgact aactatgcaa gtattactag gaagattcca tttgcagaat ttaagatttg      180
ttggttccta aaattctcga aagctccttg aatttttgat gccaatcact ttgaatgtgt      240
tctttttgcc tccttaaagt taaccttatt tggagtaaat attgatcaaa ttagtataag      300
taactgtgta aggcttcacg tctccatcaa tcatcctgaa caatcactgc tttgccttaa      360
acaaacttgt taattattta taagtttttt tttatgaaac acaactttca ttaatactca      420
aacattccaa ctacaaataa ggaaggagtt taaccaaact ctaacaacaa ataataaagc      480
atacaagcta aaagtagaga aacctctaag atagaatgac agcgaactcg aagcatggct      540
cgaatgcgtc ggagcaagac tcacagcagt gctagaggct tgaaatttag tcactttgta      600
tcgtgacgtt aagatccaat ccgcacctcg gaatatcgtc gaaacgacat ccgttgcatc      660
ttcaggcccc gaacggaccg ctagacaata tgaacaaacg gctatagata aagatacaca      720
cctccattta gtgtttgggg ggaaaacatt tctcataact gaggcatggg gtaatacgac      780
tcgcatctcc tgagagaagt atgatagtga tgaaagtggt gtagattgtc ccgataaacc      840
caccggtaaa tagaaacttc gaaaactctt cttataagag agataaggtg ttgtatgcat      900
atcaacagtt tcggtaatat tttcagtgaa cccgccgaaa aatattagca agttggacca      960
aatgaccaaa ctccccccaca caaatgtggg ctttgaaacc gacagacttc taagaaatgg   1020
gctgaccttt ttataaccct taatgggcca ggcccagata gttatgttgc tagggtttgg     1080
gtcacaaaat tgtacgccgc cgaggctagt gtggaggaga tgaagagcgc ggcggggctg     1140
aagctggtct catcggagtg aacggtttgc gcagcaaagc agatcggaga agagatgtag     1200
cctttgatag tacagaagct ctcgccggag taacagtcaa gatagacgtc tgacggagta     1260
atgatgatga gggcgtgaag aggaaagcac aacctcattg                           1300

<210>    5
<211>  390
<212> DNA
<213> Unknown

<220>
<223> Marker 5

<400>    5
ctctgcaata ttgtccttga tgagtttatt gtctcccttc tttttcagta aattcagttt       60
cgttttattt atctattgaa tttattgtcg ctattgaatt ttctgacgta tttctctgcg      120
atcactcaat ttactgtctc tgttgagttt ctcattcttc ccattcagaa tatatgtaga      180
aacaacaatt caatataagt catctgttcg ctctatcata gtagcgtaaa ggtatctttc      240
caaattgact tggcatccat attagagaga cgtcaatgaa tataagtagt atttacaact      300
aaattcgtct gattttacaa atgcttccaa gcgtacgtgt ataccaatgt tcgcctaaag      360
ataaatgcca aggttggtgt actgaattgc                                      390

<210>    6
<211>  300
<212> DNA
<213> Unknown

<220>
<223> Marker 6

<400>    6
cgatctcaca ctaactacgc ttcaccaaac aaaaagatca caatcaaatc tcatcatcct       60
acttaccaat ttaggccacg catcaatcgc acaagcttca actgtatcca aaaggcattc      120
aaacgcaccg tgctgcaaca aattagcaac aatgtttaac gtaatctcgc tacaagcatg      180
```

-continued

SEQUENCE LISTING

```
catgataacg aaacgagatc ttagatacaa acaacatctt aaataaattt aatcaaatta      240
tcgacaatgt ttaatgtaat cgctacaatc atgcatgatg acgaaacgag atctcagatt      300

<210>    7
<211> 2713
<212> DNA
<213> Unknown

<220>
<223> Marker 7

<400>    7
ttatagaagg cctgtgtacg acaacaaaga ggttttgaca cgttccaaca aatcccacat       60
cctgttgaca ccgttccggc aaaccagagg gaagcgattc actttagcac ttcgaatgaa      120
gtggctggat gagtatttgg cacacgcgtc aggcttttta gcacctttgt aagctttgca      180
gatgtagctt atgaagttct cataatcctg caatgaacac acagaaaaaa actgtggtga      240
gttcagagcc aagaaatatc aagcacacac acacacaaaa actttatgtt cccattgatc      300
acatccattt tctattgatc atgcctctca tgaagacact tcacttctcg tctgctaact      360
acagttcaca agaacaataa gataccacat ttggtaatcg caacatacat ttgacccaaa      420
aaaatggtaa gtcaattaat tttctccacg ctaatctatg ataaccctat aaaacatgtc      480
ttcctcatta gtttagttaa ctagaaagat gacccaactc tctaaataca ctaaatccaa      540
agtgttgcac aaccgaattc caaatcagtc ataagtatga atgactaaca agttaatata      600
gacacatcat tcataaacag ggagtaagag agcgtaaatt agtctaagta agaactcagt      660
agaatctaaa aaggatccta ttccaaacga acctcataaa gcggctgacc atcaaccact      720
acccagggaa cgtactgatg aggaggctga agtgcgctcg tttctgcagc atacttcaac      780
tcaagctgca gcaaatggaa acgattagtg aggaatgcaa cggaagcttc cgcttccgaa      840
caagaacata gtacataaag agaaggacac taagtacctt gtctccatgt ccactgctga      900
ggcaatcgga aacaggttta gagttgagat tgagcttctg ataacaagtc tcccacttgt      960
cgtacttgtg ctcagtcacc aaactctcaa cacagtggat aaacgggaaa tgatcgctct     1020
acaaaataaa aatgtaacga tctcacacta actacgcttc accaaacaaa aagatcacaa     1080
tcaaatctca tcatcctact taccaattta ggccacgcat caatcgcaca agcttcaact     1140
gtatccaaaa ggcattcaaa cgcaccgtgc tgcaacaaat tagcaacaat gtttaacgta     1200
atctcgctac aagcatgcat gataacgaaa cgagatctta gatacaaaca acatcttaaa     1260
taaatttaat caaattatcg acaatgttta atgtaatcgc tacaatcatg catgatgacg     1320
aaacgagatc tcagattcaa acaacaccac aatacaaatt gaagctctaa tttaatcaaa     1380
tcaggataca tcggaaaggt gtgagaagac ctggcaaacg gcagtgacat tatcggagcg     1440
gagcttggtg ttaccccacg gagatagatg gagatcgacg attgatatga gatcgtcttc     1500
gaagagcttc gtgaggtggt taacgatgaa ggaagaacag tacggacata gagactcgta     1560
gtacagtccc agcgacactt tcggagaaga tggcaggtca gatgatgatg acgatgatga     1620
tacgaagaag atcagagaaa cgtagcagaa taggagaaga agaagcttgc tcgtcgaaat     1680
cgacgccatg attgcaaaga gaagcaacct ctgttgtatc gtcttcgtcc tcttctctta     1740
ataacacgca tctcgatatg ctcggtgcga aacagatgac aataaccgat aaggcccgtc     1800
tcattctttg tgtgggcctt gttcaaagcc taaatactaa ttataaaatt tcataaaagc     1860
ccaaacgttt ataacaaagg ctccgaatac ttagtaaaat ttcttttgga ccaagtgcaa     1920
atatacatca aattagctac attaattttt gggttaagca gttgaccgag aattaaagag     1980
tgacaatata catcaaagct tggaatcaat ctcatacatg tgatgaacta gaggaccaat     2040
aaaatacttg tcatgtccat tgcttaggca aaggagggac atggattata taacctcatg     2100
tatacagatt atatatcaaa tgaaaatttt aggctattgg agtacgtgaa ggatttgatc     2160
aacaagactg agactgacga cgaggtaagc aagttgggta ggatgaatgt cgtcccagaa     2220
aaggtagtcg ttagcgtcgg gacaagtccg agttaaagga ttgcacaagt atgatagctc     2280
cagctctcct gttccgcagc atcctctcgt tgtctccttt attcctgtcc ctttcgaaaa     2340
aatcgattca gaccacgaaa aaatgcacgg tatatggcta tataacaaac tgtagactca     2400
taacctgtaa tgcgagcaca ctggattata aactcacctt agttattgta aaattaatct     2460
ttcgacttaa ttatatgaaa tgacgtcaac ataaaaatag atataatgaa aaataatatg     2520
tatcatagtg atttgtgcta ttatcatcga tatcatcatg tttaaaccaa caaatacata     2580
gttttttttt agcaaataca tatattatta acgaaaaaaa attatatata gtaatgtttt     2640
aattgttgga tagccaacaa gtataatacg taaattagca aatgcaaatg agttctatat     2700
ccagccaagc cac                                                        2713

<210>    8
<211>   22
<212> DNA
<213> Artificial Sequence

<220>
<223> primer

<400>    8
cggtcttagt tgatttctca ag                                                22

<210>    9
<211>   21
<212> DNA
<213> Artificial Sequence

<220>
<223> primer
```

-continued

SEQUENCE LISTING

<400> 9
gatcaccctg tactagcaat c 21

<210> 10
<211> 21
<212> DNA
<213> Artificial Sequence

<220>
<223> primer

<400> 10
agtagggagt aaaccaacga g 21

<210> 11
<211> 21
<212> DNA
<213> Artificial Sequence

<220>
<223> primer

<400> 11
ccacgagtgc atattaggtt g 21

<210> 12
<211> 20
<212> DNA
<213> Artificial Sequence

<220>
<223> primer

<400> 12
gtgctccgtc aagattcgac 20

<210> 13
<211> 23
<212> DNA
<213> Artificial Sequence

<220>
<223> primer

<400> 13
ggacctaatg aatcgagagc tac 23

<210> 14
<211> 21
<212> DNA
<213> Artificial Sequence

<220>
<223> primer

<400> 14
gcatcactaa gtcaagcaac t 21

<210> 15
<211> 21
<212> DNA
<213> Artificial Sequence

<220>
<223> primer

<400> 15
caatgaggtt gtgctttcct c 21

<210> 16
<211> 22
<212> DNA
<213> Artificial Sequence

<220>
<223> primer

-continued

SEQUENCE LISTING

<400> 16
ctctgcaata ttgtccttga tg 22

<210> 17
<211> 20
<212> DNA
<213> Artificial Sequence

<220>
<223> primer

<400> 17
gcaattcagt acaccaacct 20

<210> 18
<211> 21
<212> DNA
<213> Artificial Sequence

<220>
<223> primer

<400> 18
cgatctcaca ctaactacgc t 21

<210> 19
<211> 22
<212> DNA
<213> Artificial Sequence

<220>
<223> primer

<400> 19
aatctgagat ctcgtttcgt ca 22

<210> 20
<211> 22
<212> DNA
<213> Artificial Sequence

<220>
<223> primer

<400> 20
ttatagaagg cctgtgtacg ac 22

<210> 21
<211> 21
<212> DNA
<213> Artificial Sequence

<220>
<223> primer

<400> 21
gtggcttggc tggatataga a 21

<210> 22
<211> 1176
<212> DNA
<213> Unknown

<220>
<223> Marker 1a

<400> 22
cggtccttag ttgatttctc aagtttgggt gtttgtccaa tcatctcttg gtacagttga 60
agcaaaagct tcatctctgc atataatact cagaacaatc aataatttta aaaagaaaac 120
aacagagtgc tataatgaga gagagagaga gagagagaga gactcactct cttgaatttc 180
gactgctgcc ttgcagtttc tgaagtcggg agctcgtagt acctatacaa ttaccagaac 240
atatactctc cgttgatatc taattaattc cacaaacaga gagaagagta gtggagattt 300
catacctcga gaacgtgagg gcgaagatcc ttgacaagga gacgcatctt gtagtagttg 360
gagttctcca ccttcagatt cccttccagc cccctctttc tccccccttga cgacggatct 420
gacggagcca cctgagctcc tcctatatgt ggccgactcg gaaccggcgg gttatctaag 480
tccatcgccg gcgaagatct ctgatctgct gcagctgctg taggaagcgg gagagatgaa 540

-continued

SEQUENCE LISTING

```
gtagcggaag gaggaggagg agttgccgcg gaggtcgatt tctccatttt caaaaagggg      600
gttttctcaa ccgtaacacc ccagcacggg acgcagcagc cgggaactta aaacgaccgc      660
gttgtaagaa atctactgat tcggttaggg cctacttggg ggcccattat ctttttctt      720
tgtctaaacg gcccgtctgt atccgatgac catcatatag aagggtaaat catcaagtaa      780
caacaacact gcaacagaca agggacatat gtagctgaac agagaactct ctattcatta      840
gactgagata tatgttcata ataaattaag tcaaatcctg cataatagct caaagctgga      900
tttaatcatt cataattcca tgaatttttt ttacatagat atagtcttca gtttgacccc      960
aaaaaaaaaa aatagtcttc atatactcat ctctccaaag tgattgctag tacagggtga     1020
tcatcttcta atcttcacaa caagtcaagc atgagctgtt ccagtaattc atttagaatc     1080
agttcactag tctcaaagcc aatgcactca acctcacttc taacgtcatc taaccagttt     1140
ccgcgtttat ccatgtcttc tctaatgatt tggtcc                               1176

<210>   23
<211>  265
<212> DNA
<213> Unknown

<220>
<223> Marker 2a

<400>   23
gaacccctct cggaccggga ataagattct tggtttttcg gttaaagtag ggagtaaacc       60
aacgagtgta aatatcttcc ccaagccgtt ccgggatgat gtgcaaggta aaccaagtga      120
tggctatggg gacaaggaaa gaaacaaaat gttcctgcat gaaaatattg aagtttgatg      180
caaacccaca aatttggtat atatttcaaa gttattggtt cgtgttcaaa cgggtatatg      240
ctaacaacct aatatgcact cgtgg                                            265

<210>   24
<211> 1659
<212> DNA
<213> Unknown

<220>
<223> Marker 3a

<400>   24
gtgctccgtc aagattcgac gatcgtgttt tgtttccctt tttactttaa ctctcttcac       60
tcttcttcct tcattctcct cttctgatgg gaagccatag caacgcggag aaagatgaat      120
ccgccaccga gacggatgct acaacacggc agggatctct ctctgttaca gagtccaaca      180
ccgattgcga cgcagacgtc ttgcctcctc ctcctcctgc ggacgtgagt caattcgaag      240
aaggagagaa agttttagcc aaccacaaag gtcgtttcta cgaagccaag gtaatgttat      300
ttttgtctaa aattggaatg ttgtttgtgc ttttgtgttt aaaatttgat ctttgtttta      360
tgttttcagg ttcttgaaat tgcatttaaa gacaatgaat ggaactatta tgtgcattac      420
attgtaagtt tagattttat tttgttttgc gtaaccacga atctctgtaa aagcataaac      480
aaataaaaca catttattgt taatgctgcc gttattatat ttttgccgtt ttcaatatgt      540
aatcttttgt attttctttg gtttttacag ggttggaaca aaaggttagt agaccatccg      600
acagtactgt cacttactgc cggcttttta ttgtctgaat aatctttctg tacattgcat      660
catcggtctg aataatcatt ctgctgctaa atcaaaacgt ttgccaagat tacaagtttt      720
ttttgtttct aatgcattga taatttcatg gtttgattat tgttgtatat ctttgtaatg      780
attagttatt tgtatggaca gttgggacga atggataggt catgattgtg tgttgaaaca      840
caccgaggag aatattaagg aacagggtat taagcaagga gtcaagagtg ctatggcttg      900
gagagtgtcc aaggtgaaac ctagatgccc taatggtcag tgttctgggt cttttattag      960
aggctttgtt gcatgcttta tagatcatat gctagatatt atcatcattc tcttgttaat     1020
atattttgca gttgctagag gaagaaagcg gaagcaagat tctgttgata cactagtctc     1080
tccaatggtg tggattttcc tttcattttt ctctagattc caagtttctt tctattgttt     1140
tctgatcagt ttttgcctga ttgtttttgt tgtttgctgg atacaggagg agaatttggt     1200
tgctacagac aacctttttaa ctttcaatat cccgtcagcg ttgaggaagc aactcatcga     1260
cgattatgaa ttcgttactc agatgcaaaa ggtagctctc gattcattag gtccatatat     1320
caaggaattt atcagtgaca tttttgtaa catttatgtg agcagcttgt ggaacttcct     1380
cgctcgccta atgtggatga tatcttgaag aagtacactg acagcaaaat gaagaaagat     1440
ggcaggtaag cgctttgtta atgtcatttt caacagttaa agagttattt cagtactttc     1500
ttttggtgag gttatgtagg gtaagcaatt cagtagagga gattctgaaa ggtttgcgtt     1560
gctactttga caatgctttg ccggtgatgt tactttacaa caatgagcgg aagcagtatg     1620
aggaaaacgt atctgagggt gtatctccct caactgtgt                            1659

<210>   25
<211> 1399
<212> DNA
<213> Unknown

<220>
<223> Marker 4a

<400>   25
tcaacatata agtacaaatc tagcaaccga ctactattca aaaccagagt cttttgcatc       60
actaagtcaa gcaactttga tctcttggtt ttaagtttca aagaagctat ctttggacgt      120
ggattgtttg acagaagtat acatctttgg actaagtctg atagaactag tagagaacct      180
```

-continued

SEQUENCE LISTING

```
cgactaacta tgcaagtatt actaggaaga ttccatttgc agaatttaag atttgttggt      240
tcctaaaatt ctcgaaagct ccttgaattt ttgatgccaa tcactttgaa tgtgttcttt      300
ttgcctcctt aaagttaacc ttatttggag taaatattga tcaaattagt ataagtaact      360
gtgtaaggct tcacgtctcc atcaatcatc ctgaacaatc actgctttgc cttaaacaaa      420
cttgttaatt atttataagt ttttttttat gaaacacaac tttcattaat actcaaacat      480
tccaactaca aataaggaag gagtttaacc aaactctaac aacaaataat aaagcataca      540
agctaaaagt agagaaacct ctaagataga atgacagcga actcgaagca tggctcgaat      600
gcgtcggagc aagactcaca gcagtgctag aggcttgaaa tttagtcact ttgtatcgtg      660
acgttaagat ccaatccgca cctcggaata tcgtcgaaac gacatccgtt gcatcttcag      720
gccccgaacg gaccgctaga caatatgaac aaacggctat agataaagat acacacctcc      780
atttagtgtt tggggggaaa acatttctca taactgaggc atggggtaat acgactcgca      840
tctcctgaga gaagtatgat agtgatgaaa gtggtgtaga ttgtcccgat aaacccaccg      900
gtaaatagaa acttcgaaaa ctcttcttat aagagagata aggtgttgta tgcatatcaa      960
cagtttcggt aatattttca gtgaacccgc cgaaaaatat tagcaagttg gaccaaatga     1020
ccaaactccc ccacacaaat gtgggctttg aaaccgacag acttctaaga aatgggctga     1080
ccttttttata acccttaatg ggccaggccc agatagttat gttgctaggg tttgggtcac     1140
aaaattgtac gccgccgagg ctagtgtgga ggagatgaag agcgcggcgg ggctgaagct     1200
ggtctcatcg gagtgaacgg tttgcgcagc aaagcagatc ggagaagaga tgtagccttt     1260
gatagtacag aagctctcgc cggagtaaca gtcaagatag acgtctgacg gagtaatgat     1320
gatgagggcg tgaagaggaa agcacaacct cattgtacct cgtgcttttt gaactgctcg     1380
tcggatcaaa tgtggaacc                                                  1399

<210>  26
<211>  627
<212> DNA
<213> Unknown

<220>
<223> Marker 5a

<400>  26
ttttcaggta gttccactct catattatgt atgttgagtt tactgtccct attgagtttg       60
tgcaatttcc tatatatttc tctgcaatat tgtccttgat gagtttattg tctcccttct      120
ttttcagtaa attcagtttc gttttattta tctattgaat ttattgtcgc tattgaattt      180
tctgacgtat ttctctgcga tcactcaatt tactgtctct gttgagtttc tcattcttcc      240
cattcagaat atatgtagaa acaacaattc aatataagtc atctgttcgc tctatcatag      300
tagcgtaaag gtatctttcc aaattgactt ggcatcccata ttagagagac gtcaatgaat     360
ataagtagta tttacaacta aattcgtctg attttacaaa tgcttccaag cgtacgtgta      420
taccaatgtt cgcctaaaga taaatgccaa ggttggtgta ctgaattgct tgttaactat      480
ggagcgttca ccagcaatgc cattagtaac acaagttcct agcattattg ctgggatgga      540
tgtaccatca gttgatgcga ttgtgagctc catacaatgg ccactcgtat caaaataaag      600
ggcatgtgtg tatgcgtaca caattgt                                          627

<210>  27
<211> 800
<212> DNA
<213> Unknown

<220>
<223> Marker 6a

<400>  27
atgaggaggc tgaagtgcgc tcgtttctgc agcatacttc aactcaagct gcagcaaatg       60
gaaacgatta gtgaggaatg caacggaagc ttccgcttcc gaacaagaac atagtacata      120
aagagaagga cactaagtac cttgtctcca tgtccactgc tgaggcaatc ggaaacaggt      180
ttagagttga gattgagctt ctgataacaa gtctcccact tgtcgtactt gtgctcagtc      240
accaaactct caacacagtg gataaacggg aaatgatcgc tctacaaaat aaaaatgtaa      300
cgatctcaca ctaactacgc ttcaccaaac aaaaagatca caatcaaatc tcatcatcct      360
acttaccaat ttaggccacg catcaatcgc acaagcttca actgtatcca aaaggcattc      420
aaacgcaccg tgctgcaaca aattagcaac aatgtttaac gtaatctcgc tacaagcatg      480
catgataacg aaacgagatc ttagatacaa acaacatctt aaataaattt aatcaaatta      540
tcgacaatgt ttaatgtaat cgctacaatc atgcatgatg acgaaacgag atctcagatt      600
caaacaacac cacaatacaa attgaagctc taatttaatc aaatcaggat acatcggaaa      660
ggtgtgagaa gacctggcaa acggcagtga cattatcgga gcggagcttg gtgttacccc      720
acggagatag atggagatcg acgattgata tgagatcgtc ttcgaagagc ttcgtgaggt      780
ggttaacgat gaaggaagaa                                                  800

<210>  28
<211> 2846
<212> DNA
<213> Unknown

<220>
<223> Marker 7a
```

-continued

SEQUENCE LISTING

<400> 28

```
cttacacaac ccaacaacca tacactttgt gatatataga taataattaa tacagattca      60
tcatatctcg gaatctatat agattttaga gagttatcat gttacatatc acaaaagaaa     120
gagaaggtgt tttatagaag gcctgtgtac gacaacaaag aggttttgac acgttccaac     180
aaatcccaca tcctgttgac accgttccgg caaaccagag ggaagcgatt cactttagca     240
cttcgaatga agtggctgga tgagtatttg gcacacgcgt caggcttttt agcacctttg     300
taagctttgc agatgtagct tatgaagttc tcataatcct gcaatgaaca cacagaaaaa     360
aactgtggtg agttcagagc caagaaatat caagcacaca cacacacaaa aactttatgt     420
tcccattgat cacatccatt ttctattgat catgcctctc atgaagacac ttcacttctc     480
gtctgctaac tacagttcac aagaacaata agataccaca tttggtaatc gcaacataca     540
tttgacccaa aaaaatggta agtcaattaa ttttctccac gctaatctat gataacccta     600
taaaacatgt cttcctcatt agtttagtta actagaaaga tgacccaact ctctaaatac     660
actaaatcca aagtgttgca caaccgaatt ccaaatcagt cataagtatg aatgactaac     720
aagttaatat agacacatca ttcataaaca gggagtaaga gagcgtaaat tagtctaagt     780
aagaactcag tagaatctaa aaaggatcct attccaaacg aacctcataa agcggctgac     840
catcaaccac tacccaggga acgtactgat gaggaggctg aagtgcgctc gtttctgcag     900
catacttcaa ctcaagctgc agcaaatgga aacgattagt gaggaatgca acggaagctt     960
ccgcttccga acaagaacat agtacataaa gagaaggaca ctaagtacct tgtctccatg    1020
tccactgctg aggcaatcgg aaacaggttt agagttgaga ttgagcttct gataacaagt    1080
ctcccacttg tcgtacttgt gctcagtcac caaactctca acacagtgga taaacgggaa    1140
atgatcgctc tacaaaataa aaatgtaacg atctcacact aactacgctt caccaaacaa    1200
aaagatcaca atcaaatctc atcatcctac ttaccaattt aggccacgca tcaatcgcac    1260
aagcttcaac tgtatccaaa aggcattcaa acgcaccgtg ctgcaacaaa ttagcaacaa    1320
tgtttaacgt aatctcgcta caagcatgca tgataacgaa acgagatctt agatacaaac    1380
aacatcttaa ataaatttaa tcaaattatc gacaatgttt aatgtaatcg ctacaatcat    1440
gcatgatgac gaaacgagat ctcagattca aacaacacca caatacaaat tgaagctcta    1500
atttaatcaa atcaggatac atcggaaagg tgtgagaaga cctggcaaac ggcagtgaca    1560
ttatcggagc ggagcttggt gttaccccac ggagatagat ggagatcgac gattgatatg    1620
agatcgtctt cgaagagctt cgtgaggtgg ttaacgatga aggaagaaca gtacggacat    1680
agagactcgt agtacagtcc cagcgacact ttcggagaag atggcaggtc agatgatgat    1740
gacgatgatg atacgaagaa gatcagagaa acgtagcaga ataggagaag aagaagcttg    1800
ctcgtcgaaa tcgacgccat gattgcaaag agaagcaacc tctgttgtat cgtcttcgtc    1860
ctcttctctt aataacacgc atctcgatat gctcggtgcg aaacagatga caataaccga    1920
taaggcccgt ctcattcttt gtgtgggcct tgttcaaagc ctaaatacta attataaaat    1980
ttcataaaag cccaaacgtt tataacaaag gctccgaata cttagtaaaa tttcttttgg    2040
accaagtgca aatatacatc aaattagcta cattaatttt tgggttaagc agttgaccga    2100
gaattaaaga gtgacaatat acatcaaagc ttggaatcaa tctcatacat gtgatgaact    2160
agaggaccaa taaaatactt gtcatgtcca ttgcttaggc aaaggaggga catggattat    2220
ataacctcat gtatacagat tatatatcaa atgaaaattt taggctattg gagtacgtga    2280
aggatttgat caacaagact gagactgacg acgaggtaag caagttgggt aggatgaatg    2340
tcgtcccaga aaaggtagtc gttagcgtcg ggacaagtcc gagttaaagg attgcacaag    2400
tatgatagct ccagctctcc tgttccgcag catcctctcg ttgtctcctt tattcctgtc    2460
cctttcgaaa aaatcgattc agaccacgaa aaaatgcacg gtatatggct atataacaaa    2520
ctgtagactc ataacctgta atgcgagcac actggattat aaactcacct tagttattgt    2580
aaaattaatc tttcgactta attatatgaa atgacgtcaa cataaaaata gatataatga    2640
aaaataatat gtatcatagt gatttgtgct attatcatcg atatcatcat gtttaaacca    2700
acaaatacat agtttttttt tagcaaatac atatattatt aacgaaaaaa aattatatat    2760
agtaatgttt taattgttgg atagccaaca agtataatac gtaaattagc aaatgcaaat    2820
gagttctata tccagccaag ccacct                                          2846
```

SEQUENCE LISTING

<160> NUMBER OF SEQ ID NOS: 28

<210> SEQ ID NO 1
<211> LENGTH: 1022
<212> TYPE: DNA
<213> ORGANISM: Unknown
<220> FEATURE:
<223> OTHER INFORMATION: Marker 1

<400> SEQUENCE: 1

```
cggtccttag ttgatttctc aagtttgggt gtttgtccaa tcatctcttg gtacagttga      60

agcaaaagct tcatctctgc atataatact cagaacaatc aataatttta aaaagaaaac     120

aacagagtgc tataatgaga gagagagaga gagagagaga gactcactct cttgaatttc     180

gactgctgcc ttgcagtttc tgaagtcggg agctcgtagt acctatacaa ttaccagaac     240

atatactctc cgttgatatc taattaattc cacaaacaga gagaagagta gtggagattt     300
```

```
catacctcga gaacgtgagg gcgaagatcc ttgacaagga gacgcatctt gtagtagttg    360

gagttctcca ccttcagatt cccttccagc cccctctttc tcccccttga cgacggatct    420

gacggagcca cctgagctcc tcctatatgt ggccgactcg gaaccggcgg gttatctaag    480

tccatcgccg gcgaagatct ctgatctgct gcagctgctg taggaagcgg gagagatgaa    540

gtagcggaag gaggaggagg agttgccgcg gaggtcgatt tctccatttt caaaaagggg    600

gttttctcaa ccgtaacacc ccagcacggg acgcagcagc cgggaactta aaacgaccgc    660

gttgtaagaa atctactgat tcggttaggg cctacttggg ggcccattat cttttttctt    720

tgtctaaacg gcccgtctgt atccgatgac catcatatag aagggtaaat catcaagtaa    780

caacaacact gcaacagaca agggacatat gtagctgaac agagaactct ctattcatta    840

gactgagata tatgttcata ataaattaag tcaaatcctg cataatagct caaagctgga    900

tttaatcatt cataattcca tgaatttttt ttacatagat atagtcttca gtttgacccc    960

aaaaaaaaaa aatagtcttc atatactcat ctctccaaag tgattgctag tacagggtga   1020

tc                                                                  1022
```

<210> SEQ ID NO 2
<211> LENGTH: 220
<212> TYPE: DNA
<213> ORGANISM: Unknown
<220> FEATURE:
<223> OTHER INFORMATION: Marker 2

<400> SEQUENCE: 2

```
agtagggagt aaaccaacga gtgtaaatat cttccccaag ccgttccggg atgatgtgca     60

aggtaaacca agtgatggct atggggacaa ggaaagaaac aaaatgttcc tgcatgaaaa    120

tattgaagtt tgatgcaaac ccacaaattt ggtatatatt tcaaagttat tggttcgtgt    180

tcaaacgggt atatgctaac aacctaatat gcactcgtgg                          220
```

<210> SEQ ID NO 3
<211> LENGTH: 1314
<212> TYPE: DNA
<213> ORGANISM: Unknown
<220> FEATURE:
<223> OTHER INFORMATION: Marker 3

<400> SEQUENCE: 3

```
gtgctccgtc aagattcgac gatcgtgttt tgtttccctt tttactttaa ctctcttcac     60

tcttcttcct tcattctcct cttctgatgg gaagccatag caacgcggag aaagatgaat    120

ccgccaccga gacggatgct acaacacggc agggatctct ctctgttaca gagtccaaca    180

ccgattgcga cgcagacgtc ttgcctcctc ctcctcctgc ggacgtgagt caattcgaag    240

aaggagagaa agttttagcc aaccacaaag gtcgtttcta cgaagccaag gtaatgttat    300

ttttgtctaa aattggaatg ttgtttgtgc ttttgtgttt aaaatttgat ctttgtttta    360

tgttttcagg ttcttgaaat tgcatttaaa gacaatgaat ggaactatta tgtgcattac    420

attgtaagtt tagattttat tttgttttgc gtaaccacga atctctgtaa aagcataaac    480

aaataaaaca catttattgt taatgctgcc gttattatat ttttgccgtt ttcaatatgt    540

aatcttttgt attttctttg gtttttacag ggttggaaca aaaggttagt agaccatccg    600

acagtactgt cacttactgc cggcttttta ttgtctgaat aatctttctg tacattgcat    660

catcggtctg aataatcatt ctgctgctaa atcaaaacgt ttgccaagat tacaagtttt    720
```

-continued ttttgtttct aatgcattga taatttcatg gtttgattat tgttgtatat ctttgtaatg 780
attagttatt tgtatggaca gttgggacga atggataggt catgattgtg tgttgaaaca 840
caccgaggag aatattaagg aacagggtat taagcaagga gtcaagagtg ctatggcttg 900
gagagtgtcc aaggtgaaac ctagatgccc taatggtcag tgttctgggt cttttattag 960
aggctttgtt gcatgcttta tagatcatat gctagatatt atcatcattc tcttgttaat 1020
atattttgca gttgctagag gaagaaagcg gaagcaagat tctgttgata cactagtctc 1080
tccaatggtg tggattttcc tttcattttt ctctagattc caagtttctt tctattgttt 1140
tctgatcagt ttttgcctga ttgtttttgt tgtttgctgg atacaggagg agaatttggt 1200
tgctacagac aaccttttaa ctttcaatat cccgtcagcg ttgaggaagc aactcatcga 1260
cgattatgaa ttcgttactc agatgcaaaa ggtagctctc gattcattag gtcc 1314

<210> SEQ ID NO 4
<211> LENGTH: 1300
<212> TYPE: DNA
<213> ORGANISM: Unknown
<220> FEATURE:
<223> OTHER INFORMATION: Marker 4

<400> SEQUENCE: 4
gcatcactaa gtcaagcaac tttgatctct tggttttaag tttcaaagaa gctatctttg 60
gacgtggatt gtttgacaga agtatacatc tttggactaa gtctgataga actagtagag 120
aacctcgact aactatgcaa gtattactag gaagattcca tttgcagaat ttaagatttg 180
ttggttccta aaattctcga aagctccttg aatttttgat gccaatcact ttgaatgtgt 240
tctttttgcc tccttaaagt taaccttatt tggagtaaat attgatcaaa ttagtataag 300
taactgtgta aggcttcacg tctccatcaa tcatcctgaa caatcactgc tttgccttaa 360
acaaacttgt taattattta taagtttttt tttatgaaac acaactttca ttaatactca 420
aacattccaa ctacaaataa ggaaggagtt taaccaaact ctaacaacaa ataataaagc 480
atacaagcta aaagtagaga aacctctaag atagaatgac agcgaactcg aagcatggct 540
cgaatgcgtc ggagcaagac tcacagcagt gctagaggct tgaaatttag tcactttgta 600
tcgtgacgtt aagatccaat ccgcacctcg gaatatcgtc gaaacgacat ccgttgcatc 660
ttcaggcccc gaacggaccg ctagacaata tgaacaaacg gctatagata aagatacaca 720
cctccattta gtgtttgggg ggaaaacatt tctcataact gaggcatggg gtaatacgac 780
tcgcatctcc tgagagaagt atgatagtga tgaaagtggt gtagattgtc ccgataaacc 840
caccggtaaa tagaaacttc gaaaactctt cttataagag agataaggtg ttgtatgcat 900
atcaacagtt tcggtaatat tttcagtgaa cccgccgaaa aatattagca agttggacca 960
aatgaccaaa ctcccccaca caaatgtggg ctttgaaacc gacagacttc taagaaatgg 1020
gctgaccttt ttataaccct taatgggcca ggcccagata gttatgttgc tagggtttgg 1080
gtcacaaaat tgtacgccgc cgaggctagt gtggaggaga tgaagagcgc ggcggggctg 1140
aagctggtct catcggagtg aacggtttgc gcagcaaagc agatcggaga agagatgtag 1200
cctttgatag tacagaagct ctcgccggag taacagtcaa gatagacgtc tgacggagta 1260
atgatgatga gggcgtgaag aggaaagcac aacctcattg 1300

<210> SEQ ID NO 5
<211> LENGTH: 390
<212> TYPE: DNA
<213> ORGANISM: Unknown

-continued

<220> FEATURE:
<223> OTHER INFORMATION: Marker 5

<400> SEQUENCE: 5
ctctgcaata ttgtccttga tgagtttatt gtctcccttc tttttcagta aattcagttt 60
cgttttattt atctattgaa tttattgtcg ctattgaatt ttctgacgta tttctctgcg 120
atcactcaat ttactgtctc tgttgagttt ctcattcttc ccattcagaa tatatgtaga 180
aacaacaatt caatataagt catctgttcg ctctatcata gtagcgtaaa ggtatctttc 240
caaattgact tggcatccat attagagaga cgtcaatgaa tataagtagt atttacaact 300
aaattcgtct gattttacaa atgcttccaa gcgtacgtgt ataccaatgt tcgcctaaag 360
ataaatgcca aggttggtgt actgaattgc 390

<210> SEQ ID NO 6
<211> LENGTH: 300
<212> TYPE: DNA
<213> ORGANISM: Unknown
<220> FEATURE:
<223> OTHER INFORMATION: Marker 6

<400> SEQUENCE: 6
cgatctcaca ctaactacgc ttcaccaaac aaaaagatca caatcaaatc tcatcatcct 60
acttaccaat ttaggccacg catcaatcgc acaagcttca actgtatcca aaaggcattc 120
aaacgcaccg tgctgcaaca aattagcaac aatgtttaac gtaatctcgc tacaagcatg 180
catgataacg aaacgagatc ttagatacaa acaacatctt aaataaattt aatcaaatta 240
tcgacaatgt ttaatgtaat cgctacaatc atgcatgatg acgaaacgag atctcagatt 300

<210> SEQ ID NO 7
<211> LENGTH: 2713
<212> TYPE: DNA
<213> ORGANISM: Unknown
<220> FEATURE:
<223> OTHER INFORMATION: Marker 7

<400> SEQUENCE: 7
ttatagaagg cctgtgtacg acaacaaaga ggttttgaca cgttccaaca aatcccacat 60
cctgttgaca ccgttccggc aaaccagagg gaagcgattc actttagcac ttcgaatgaa 120
gtggctggat gagtatttgg cacacgcgtc aggcttttta gcacctttgt aagctttgca 180
gatgtagctt atgaagttct cataatcctg caatgaacac acagaaaaaa actgtggtga 240
gttcagagcc aagaaatatc aagcacacac acacacaaaa actttatgtt cccattgatc 300
acatccattt tctattgatc atgcctctca tgaagacact tcacttctcg tctgctaact 360
acagttcaca agaacaataa gataccacat ttggtaatcg caacatacat ttgacccaaa 420
aaaatggtaa gtcaattaat tttctccacg ctaatctatg ataaccctat aaaacatgtc 480
ttcctcatta gtttagttaa ctagaaagat gacccaactc tctaaataca ctaaatccaa 540
agtgttgcac aaccgaattc caaatcagtc ataagtatga atgactaaca agttaatata 600
gacacatcat tcataaacag ggagtaagag agcgtaaatt agtctaagta agaactcagt 660
agaatctaaa aaggatccta ttccaaacga acctcataaa gcggctgacc atcaaccact 720
acccagggaa cgtactgatg aggaggctga agtgcgctcg tttctgcagc atacttcaac 780
tcaagctgca gcaaatggaa acgattagtg aggaatgcaa cggaagcttc cgcttccgaa 840
caagaacata gtacataaag agaaggacac taagtacctt gtctccatgt ccactgctga 900

-continued

```
ggcaatcgga aacaggttta gagttgagat tgagcttctg ataacaagtc tcccacttgt    960

cgtacttgtg ctcagtcacc aaactctcaa cacagtggat aaacgggaaa tgatcgctct   1020

acaaaataaa aatgtaacga tctcacacta actacgcttc accaaacaaa aagatcacaa   1080

tcaaatctca tcatcctact taccaattta ggccacgcat caatcgcaca agcttcaact   1140

gtatccaaaa ggcattcaaa cgcaccgtgc tgcaacaaat tagcaacaat gtttaacgta   1200

atctcgctac aagcatgcat gataacgaaa cgagatctta gatacaaaca acatcttaaa   1260

taaatttaat caaattatcg acaatgttta atgtaatcgc tacaatcatg catgatgacg   1320

aaacgagatc tcagattcaa acaacaccac aatacaaatt gaagctctaa tttaatcaaa   1380

tcaggataca tcggaaaggt gtgagaagac ctggcaaacg gcagtgacat tatcggagcg   1440

gagcttggtg ttaccccacg gagatagatg gagatcgacg attgatatga gatcgtcttc   1500

gaagagcttc gtgaggtggt taacgatgaa ggaagaacag tacggacata gagactcgta   1560

gtacagtccc agcgacactt tcggagaaga tggcaggtca gatgatgatg acgatgatga   1620

tacgaagaag atcagagaaa cgtagcagaa taggagaaga agaagcttgc tcgtcgaaat   1680

cgacgccatg attgcaaaga gaagcaacct ctgttgtatc gtcttcgtcc tcttctctta   1740

ataacacgca tctcgatatg ctcggtgcga aacagatgac aataaccgat aaggcccgtc   1800

tcattctttg tgtgggcctt gttcaaagcc taaatactaa ttataaaatt tcataaaagc   1860

ccaaacgttt ataacaaagg ctccgaatac ttagtaaaat ttcttttgga ccaagtgcaa   1920

atatacatca aattagctac attaattttt gggttaagca gttgaccgag aattaaagag   1980

tgacaatata catcaaagct tggaatcaat ctcatacatg tgatgaacta gaggaccaat   2040

aaaatacttg tcatgtccat tgcttaggca aaggagggac atggattata taacctcatg   2100

tatacagatt atatatcaaa tgaaaatttt aggctattgg agtacgtgaa ggatttgatc   2160

aacaagactg agactgacga cgaggtaagc aagttgggta ggatgaatgt cgtcccagaa   2220

aaggtagtcg ttagcgtcgg gacaagtccg agttaaagga ttgcacaagt atgatagctc   2280

cagctctcct gttccgcagc atcctctcgt tgtctccttt attcctgtcc ctttcgaaaa   2340

aatcgattca gaccacgaaa aaatgcacgg tatatggcta tataacaaac tgtagactca   2400

taacctgtaa tgcgagcaca ctggattata aactcacctt agttattgta aaattaatct   2460

ttcgacttaa ttatatgaaa tgacgtcaac ataaaaatag atataatgaa aaataatatg   2520

tatcatagtg atttgtgcta ttatcatcga tatcatcatg tttaaaccaa caaatacata   2580

gtttttttt agcaaataca tatattatta acgaaaaaaa attatatata gtaatgtttt   2640

aattgttgga tagccaacaa gtataatacg taaattagca aatgcaaatg agttctatat   2700

ccagccaagc cac                                                      2713


<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8

cggtcttagt tgatttctca ag                                              22


<210> SEQ ID NO 9
<211> LENGTH: 21
<212> TYPE: DNA
<213> ORGANISM: Artificial Sequence
```

```
<220> FEATURE:
<223> OTHER INFORMATION: primer

<400> SEQUENCE: 9

gatcaccctg tactagcaat c                                              21


<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10

agtagggagt aaaccaacga g                                              21


<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11

ccacgagtgc atattaggtt g                                              21


<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12

gtgctccgtc aagattcgac                                                20


<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13

ggacctaatg aatcgagagc tac                                            23


<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14

gcatcactaa gtcaagcaac t                                              21


<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15

caatgaggtt gtgctttcct c                                              21
```

-continued

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
ctctgcaata ttgtccttga tg 22

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gcaattcagt acaccaacct 20

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
cgatctcaca ctaactacgc t 21

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
aatctgagat ctcgtttcgt ca 22

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
ttatagaagg cctgtgtacg ac 22

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
gtggcttggc tggatataga a 21

<210> SEQ ID NO 22
<211> LENGTH: 1176
<212> TYPE: DNA
<213> ORGANISM: Unknown
<220> FEATURE:
<223> OTHER INFORMATION: Marker 1a

<400> SEQUENCE: 22

```
cggtccttag ttgatttctc aagtttgggt gtttgtccaa tcatctcttg gtacagttga     60
agcaaaagct tcatctctgc atataatact cagaacaatc aataatttta aaaagaaaac    120
aacagagtgc tataatgaga gagagagaga gagagagaga gactcactct cttgaatttc    180
gactgctgcc ttgcagtttc tgaagtcggg agctcgtagt acctatacaa ttaccagaac    240
atatactctc cgttgatatc taattaattc cacaaacaga gagaagagta gtggagattt    300
catacctcga gaacgtgagg gcgaagatcc ttgacaagga gacgcatctt gtagtagttg    360
gagttctcca ccttcagatt cccttccagc cccctctttc tccccccttga cgacggatct    420
gacggagcca cctgagctcc tcctatatgt ggccgactcg gaaccggcgg gttatctaag    480
tccatcgccg gcgaagatct ctgatctgct gcagctgctg taggaagcgg gagagatgaa    540
gtagcggaag gaggaggagg agttgccgcg gaggtcgatt tctccatttt caaaaagggg    600
gttttctcaa ccgtaacacc ccagcacggg acgcagcagc cgggaactta aaacgaccgc    660
gttgtaagaa atctactgat tcggttaggg cctacttggg ggcccattat cttttttctt    720
tgtctaaacg gcccgtctgt atccgatgac catcatatag aagggtaaat catcaagtaa    780
caacaacact gcaacagaca agggacatat gtagctgaac agagaactct ctattcatta    840
gactgagata tatgttcata ataaattaag tcaaatcctg cataatagct caaagctgga    900
tttaatcatt cataattcca tgaatttttt ttacatagat atagtcttca gtttgacccc    960
aaaaaaaaaa aatagtcttc atatactcat ctctccaaag tgattgctag tacagggtga   1020
tcatcttcta atcttcacaa caagtcaagc atgagctgtt ccagtaattc atttagaatc   1080
agttcactag tctcaaagcc aatgcactca acctcacttc taacgtcatc taaccagttt   1140
ccgcgtttat ccatgtcttc tctaatgatt tggtcc                             1176
```

<210> SEQ ID NO 23
<211> LENGTH: 265
<212> TYPE: DNA
<213> ORGANISM: Unknown
<220> FEATURE:
<223> OTHER INFORMATION: Marker 2a

<400> SEQUENCE: 23

```
gaacccctct cggaccggga ataagattct tggtttttcg gttaaagtag ggagtaaacc     60
aacgagtgta aatatcttcc ccaagccgtt ccgggatgat gtgcaaggta aaccaagtga    120
tggctatggg gacaaggaaa gaaacaaaat gttcctgcat gaaaatattg aagtttgatg    180
caaacccaca aatttggtat atatttcaaa gttattggtt cgtgttcaaa cgggtatatg    240
ctaacaacct aatatgcact cgtgg                                          265
```

<210> SEQ ID NO 24
<211> LENGTH: 1659
<212> TYPE: DNA
<213> ORGANISM: Unknown
<220> FEATURE:
<223> OTHER INFORMATION: Marker 3a

<400> SEQUENCE: 24

```
gtgctccgtc aagattcgac gatcgtgttt tgtttccctt tttactttaa ctctcttcac     60
tcttcttcct tcattctcct cttctgatgg gaagccatag caacgcggag aaagatgaat    120
ccgccaccga gacggatgct acaacacggc agggatctct ctctgttaca gagtccaaca    180
```

-continued

```
ccgattgcga cgcagacgtc ttgcctcctc ctcctcctgc ggacgtgagt caattcgaag    240

aaggagagaa agttttagcc aaccacaaag gtcgtttcta cgaagccaag gtaatgttat    300

ttttgtctaa aattggaatg ttgtttgtgc ttttgtgttt aaaatttgat ctttgtttta    360

tgttttcagg ttcttgaaat tgcatttaaa gacaatgaat ggaactatta tgtgcattac    420

attgtaagtt tagattttat tttgttttgc gtaaccacga atctctgtaa aagcataaac    480

aaataaaaca catttattgt taatgctgcc gttattatat ttttgccgtt ttcaatatgt    540

aatcttttgt attttctttg gtttttacag ggttggaaca aaaggttagt agaccatccg    600

acagtactgt cacttactgc cggcttttta ttgtctgaat aatctttctg tacattgcat    660

catcggtctg aataatcatt ctgctgctaa atcaaaacgt ttgccaagat tacaagtttt    720

ttttgtttct aatgcattga taatttcatg gtttgattat tgttgtatat ctttgtaatg    780

attagttatt tgtatggaca gttgggacga atggataggt catgattgtg tgttgaaaca    840

caccgaggag aatattaagg aacagggtat taagcaagga gtcaagagtg ctatggcttg    900

gagagtgtcc aaggtgaaac ctagatgccc taatggtcag tgttctgggt cttttattag    960

aggctttgtt gcatgcttta tagatcatat gctagatatt atcatcattc tcttgttaat   1020

atattttgca gttgctagag gaagaaagcg gaagcaagat tctgttgata cactagtctc   1080

tccaatggtg tggattttcc tttcattttt ctctagattc caagtttctt tctattgttt   1140

tctgatcagt ttttgcctga ttgtttttgt tgtttgctgg atacaggagg agaatttggt   1200

tgctacagac aaccttttaa ctttcaatat cccgtcagcg ttgaggaagc aactcatcga   1260

cgattatgaa ttcgttactc agatgcaaaa ggtagctctc gattcattag gtccatatat   1320

caaggaattt atcagtgaca ttttttgtaa catttatgtg agcagcttgt ggaacttcct   1380

cgctcgccta atgtggatga tatcttgaag aagtacactg acagcaaaat gaagaaagat   1440

ggcaggtaag cgctttgtta atgtcatttt caacagttaa agagttattt cagtactttc   1500

ttttggtgag gttatgtagg gtaagcaatt cagtagagga gattctgaaa ggtttgcgtt   1560

gctactttga caatgctttg ccggtgatgt tactttacaa caatgagcgg aagcagtatg   1620

aggaaaacgt atctgagggt gtatctccct caactgtgt                          1659
```

```
<210> SEQ ID NO 25
<211> LENGTH: 1399
<212> TYPE: DNA
<213> ORGANISM: Unknown
<220> FEATURE:
<223> OTHER INFORMATION: Marker 4a

<400> SEQUENCE: 25

tcaacatata agtacaaatc tagcaaccga ctactattca aaaccagagt cttttgcatc     60

actaagtcaa gcaactttga tctcttggtt ttaagtttca aagaagctat ctttggacgt    120

ggattgtttg acagaagtat acatctttgg actaagtctg atagaactag tagagaacct    180

cgactaacta tgcaagtatt actaggaaga ttccatttgc agaatttaag atttgttggt    240

tcctaaaatt ctcgaaagct ccttgaattt ttgatgccaa tcactttgaa tgtgttcttt    300

ttgcctcctt aaagttaacc ttatttggag taaatattga tcaaattagt ataagtaact    360

gtgtaaggct tcacgtctcc atcaatcatc ctgaacaatc actgctttgc cttaaacaaa    420

cttgttaatt atttataagt ttttttttat gaaacacaac tttcattaat actcaaacat    480

tccaactaca aataaggaag gagtttaacc aaactctaac aacaaataat aaagcataca    540

agctaaaagt agagaaacct ctaagataga atgacagcga actcgaagca tggctcgaat    600
```

gcgtcggagc aagactcaca gcagtgctag aggcttgaaa tttagtcact ttgtatcgtg 660
acgttaagat ccaatccgca cctcggaata tcgtcgaaac gacatccgtt gcatcttcag 720
gccccgaacg gaccgctaga caatatgaac aaacggctat agataaagat acacacctcc 780
atttagtgtt tggggggaaa acatttctca taactgaggc atggggtaat acgactcgca 840
tctcctgaga gaagtatgat agtgatgaaa gtggtgtaga ttgtcccgat aaacccaccg 900
gtaaatagaa acttcgaaaa ctcttcttat aagagagata aggtgttgta tgcatatcaa 960
cagtttcggt aatattttca gtgaacccgc cgaaaaatat tagcaagttg gaccaaatga 1020
ccaaactccc ccacacaaat gtgggctttg aaaccgacag acttctaaga aatgggctga 1080
cctttttata acccttaatg ggccaggccc agatagttat gttgctaggg tttgggtcac 1140
aaaattgtac gccgccgagg ctagtgtgga ggagatgaag agcgcggcgg ggctgaagct 1200
ggtctcatcg gagtgaacgg tttgcgcagc aaagcagatc ggagaagaga tgtagccttt 1260
gatagtacag aagctctcgc cggagtaaca gtcaagatag acgtctgacg gagtaatgat 1320
gatgagggcg tgaagaggaa agcacaacct cattgtacct cgtgcttttt gaactgctcg 1380
tcggatcaaa tgtggaacc 1399

<210> SEQ ID NO 26
<211> LENGTH: 627
<212> TYPE: DNA
<213> ORGANISM: Unknown
<220> FEATURE:
<223> OTHER INFORMATION: Marker 5a

<400> SEQUENCE: 26
ttttcaggta gttccactct catattatgt atgttgagtt tactgtccct attgagtttg 60
tgcaatttcc tatatatttc tctgcaatat tgtccttgat gagtttattg tctcccttct 120
ttttcagtaa attcagtttc gttttattta tctattgaat ttattgtcgc tattgaattt 180
tctgacgtat ttctctgcga tcactcaatt tactgtctct gttgagtttc tcattcttcc 240
cattcagaat atatgtagaa acaacaattc aatataagtc atctgttcgc tctatcatag 300
tagcgtaaag gtatctttcc aaattgactt ggcatccata ttagagagac gtcaatgaat 360
ataagtagta tttacaacta aattcgtctg attttacaaa tgcttccaag cgtacgtgta 420
taccaatgtt cgcctaaaga taaatgccaa ggttggtgta ctgaattgct tgttaactat 480
ggagcgttca ccagcaatgc cattagtaac acaagttcct agcattattg ctgggatgga 540
tgtaccatca gttgatgcga ttgtgagctc catacaatgg ccactcgtat caaaataaag 600
ggcatgtgtg tatgcgtaca caattgt 627

<210> SEQ ID NO 27
<211> LENGTH: 800
<212> TYPE: DNA
<213> ORGANISM: Unknown
<220> FEATURE:
<223> OTHER INFORMATION: Marker 6a

<400> SEQUENCE: 27
atgaggaggc tgaagtgcgc tcgtttctgc agcatacttc aactcaagct gcagcaaatg 60
gaaacgatta gtgaggaatg caacggaagc ttccgcttcc gaacaagaac atagtacata 120
aagagaagga cactaagtac cttgtctcca tgtccactgc tgaggcaatc ggaaacaggt 180
ttagagttga gattgagctt ctgataacaa gtctcccact tgtcgtactt gtgctcagtc 240

-continued

```
accaaactct caacacagtg gataaacggg aaatgatcgc tctacaaaat aaaaatgtaa    300
cgatctcaca ctaactacgc ttcaccaaac aaaaagatca caatcaaatc tcatcatcct    360
acttaccaat ttaggccacg catcaatcgc acaagcttca actgtatcca aaaggcattc    420
aaacgcaccg tgctgcaaca aattagcaac aatgtttaac gtaatctcgc tacaagcatg    480
catgataacg aaacgagatc ttagatacaa acaacatctt aaataaattt aatcaaatta    540
tcgacaatgt ttaatgtaat cgctacaatc atgcatgatg acgaaacgag atctcagatt    600
caaacaacac cacaatacaa attgaagctc taatttaatc aaatcaggat acatcggaaa    660
ggtgtgagaa gacctggcaa acggcagtga cattatcgga gcggagcttg gtgttacccc    720
acggagatag atggagatcg acgattgata tgagatcgtc ttcgaagagc ttcgtgaggt    780
ggttaacgat gaaggaagaa                                                800
```

<210> SEQ ID NO 28
<211> LENGTH: 2846
<212> TYPE: DNA
<213> ORGANISM: Unknown
<220> FEATURE:
<223> OTHER INFORMATION: Marker 7a

<400> SEQUENCE: 28

```
cttacacaac ccaacaacca tacactttgt gatatataga taataattaa tacagattca     60
tcatatctcg gaatctatat agattttaga gagttatcat gttacatatc acaaaagaaa    120
gagaaggtgt tttatagaag gcctgtgtac gacaacaaag aggttttgac acgttccaac    180
aaatcccaca tcctgttgac accgttccgg caaaccagag ggaagcgatt cactttagca    240
cttcgaatga agtggctgga tgagtatttg gcacacgcgt caggcttttt agcacctttg    300
taagctttgc agatgtagct tatgaagttc tcataatcct gcaatgaaca cacagaaaaa    360
aactgtggtg agttcagagc caagaaatat caagcacaca cacacacaaa aactttatgt    420
tcccattgat cacatccatt ttctattgat catgcctctc atgaagacac ttcacttctc    480
gtctgctaac tacagttcac aagaacaata agataccaca tttggtaatc gcaacataca    540
tttgacccaa aaaaatggta agtcaattaa ttttctccac gctaatctat gataacccta    600
taaaacatgt cttcctcatt agtttagtta actagaaaga tgacccaact ctctaaatac    660
actaaatcca aagtgttgca caaccgaatt ccaaatcagt cataagtatg aatgactaac    720
aagttaatat agacacatca ttcataaaca gggagtaaga gagcgtaaat tagtctaagt    780
aagaactcag tagaatctaa aaaggatcct attccaaacg aacctcataa agcggctgac    840
catcaaccac tacccaggga acgtactgat gaggaggctg aagtgcgctc gtttctgcag    900
catacttcaa ctcaagctgc agcaaatgga aacgattagt gaggaatgca acggaagctt    960
ccgcttccga acaagaacat agtacataaa gagaaggaca ctaagtacct tgtctccatg   1020
tccactgctg aggcaatcgg aaacaggttt agagttgaga ttgagcttct gataacaagt   1080
ctcccacttg tcgtacttgt gctcagtcac caaactctca acacagtgga taaacgggaa   1140
atgatcgctc tacaaaataa aaatgtaacg atctcacact aactacgctt caccaaacaa   1200
aaagatcaca atcaaatctc atcatcctac ttaccaattt aggccacgca tcaatcgcac   1260
aagcttcaac tgtatccaaa aggcattcaa acgcaccgtg ctgcaacaaa ttagcaacaa   1320
tgtttaacgt aatctcgcta caagcatgca tgataacgaa acgagatctt agatacaaac   1380
aacatcttaa ataaatttaa tcaaattatc gacaatgttt aatgtaatcg ctacaatcat   1440
gcatgatgac gaaacgagat ctcagattca aacaacacca caatacaaat tgaagctcta   1500
```

-continued

```
atttaatcaa atcaggatac atcggaaagg tgtgagaaga cctggcaaac ggcagtgaca   1560
ttatcggagc ggagcttggt gttaccccac ggagatagat ggagatcgac gattgatatg   1620
agatcgtctt cgaagagctt cgtgaggtgg ttaacgatga aggaagaaca gtacggacat   1680
agagactcgt agtacagtcc cagcgacact ttcggagaag atggcaggtc agatgatgat   1740
gacgatgatg atacgaagaa gatcagagaa acgtagcaga ataggagaag aagaagcttg   1800
ctcgtcgaaa tcgacgccat gattgcaaag agaagcaacc tctgttgtat cgtcttcgtc   1860
ctcttctctt aataacacgc atctcgatat gctcggtgcg aaacagatga caataaccga   1920
taaggcccgt ctcattcttt gtgtgggcct tgttcaaagc ctaaatacta attataaaat   1980
ttcataaaag cccaaacgtt tataacaaag gctccgaata cttagtaaaa tttcttttgg   2040
accaagtgca aatatacatc aaattagcta cattaatttt tgggttaagc agttgaccga   2100
gaattaaaga gtgacaatat acatcaaagc ttggaatcaa tctcatacat gtgatgaact   2160
agaggaccaa taaaatactt gtcatgtcca ttgcttaggc aaaggaggga catggattat   2220
ataacctcat gtatacagat tatatatcaa atgaaaattt taggctattg gagtacgtga   2280
aggatttgat caacaagact gagactgacg acgaggtaag caagttgggt aggatgaatg   2340
tcgtcccaga aaaggtagtc gttagcgtcg ggacaagtcc gagttaaagg attgcacaag   2400
tatgatagct ccagctctcc tgttccgcag catcctctcg ttgtctcctt tattcctgtc   2460
cctttcgaaa aaatcgattc agaccacgaa aaaatgcacg gtatatggct atataacaaa   2520
ctgtagactc ataacctgta atgcgagcac actggattat aaactcacct tagttattgt   2580
aaaattaatc tttcgactta attatatgaa atgacgtcaa cataaaaata gatataatga   2640
aaaataatat gtatcatagt gatttgtgct attatcatcg atatcatcat gtttaaacca   2700
acaaatacat agtttttttt tagcaaatac atatattatt aacgaaaaaa aattatatat   2760
agtaatgttt taattgttgg atagccaaca agtataatac gtaaattagc aaatgcaaat   2820
gagttctata tccagccaag ccacct                                        2846
```

The invention claimed is:

1. A downy mildew resistant cabbage or its progeny having a downy mildew resistant gene which is positioned in the vicinity of the locus comprising one or more of the marker nucleotide sequence of SEQ ID NO. 1, SEQ ID NO. 2, SEQ ID NO. 3, SEQ ID NO. 4, SEQ ID NO: 5, SEQ ID NO. 6 or SEQ ID NO. 7; wherein the downy mildew resistant gene is found in the broccoli variety deposited under Accession Number FERM BP-22343.

2. The downy mildew resistant cabbage or its progeny according to claim 1, having a downy mildew resistant gene which is detectable by any one or more of the primer pairs having the nucleotide sequences of SEQ ID NO: 8-9, SEQ ID NO: 10-11, SEQ ID NO:12-13, SEQ ID NO: 14-15, SEQ ID NO: 16-17, SEQ ID NO: 18-19, or SEQ ID NO:20-21.

3. The downy mildew resistant cabbage or its progeny according to claim 1, wherein the downy mildew is a disease caused by *Hyaloperonospora brassicae.*

4. The downy mildew resistant cabbage or its progeny according to claim 1, wherein the downy mildew resistant cabbage plant is the cabbage variety deposited under Accession Number PERM BP-22344.

5. A seed that produces the downy mildew resistant cabbage plant of claim 4, wherein the downy mildew resistant cabbage plant is the cabbage variety deposited under Accession Number PERM BP-22344.

6. A method for breeding a downy mildew resistant cabbage, comprising crossing the down mildew resistant cabbage plant or its progeny of claim 1 with a desired cabbage plant that is susceptible to downy mildew.

7. A method for breeding downy mildew resistant cabbage, comprising introducing downy mildew resistance locus from a *Brassica oleracea* plant having resistance against downy mildew into a desired cabbage plant, wherein the downy mildew resistance being confirmed by a downy mildew resistant gene positioned in the vicinity of the locus comprising one or more of the marker nucleotide sequence of SEQ ID NO:1, SEQ ID NO: 2, SEQ ID NO: 3, SEQ ID NO: 4, SEQ ID NO: 5, SEQ ID NO: 6, or SEQ ID NO: 7; wherein the *Brassica oleracea* plant having resistance against downy mildew is the broccoli variety deposited under Accession Number FERM BP-22343.

8. The breeding method according to claim 6, wherein the *Brassica oleracea* plant having resistance against downy mildew is the cabbage variety deposited under Accession Number PERM BP-22344.

9. The breeding method according to claim 7, wherein the introduction of downy mildew resistance into desired cabbage is achieved by continuous backcross of the desired cabbage plant.

10. The breeding method according to claim 6, further comprising assaying the presence of a downy mildew resistant gene using one or more of the or primer pairs having the nucleotide sequences of SEQ ID NO: 8-9, SEQ ID NO: 10-11, SEQ ID NO:12-13, SEQ ID NO: 14-15, SEQ ID NO: 16-17, SEQ ID NO: 18-19, or SEQ ID NO: 20-21.

* * * * *